United States Patent [19]
Hafeman et al.

[11] Patent Number: 5,959,738
[45] Date of Patent: Sep. 28, 1999

[54] DETERMINATION OF LIGHT ABSORPTION PATHLENGTH IN A VERTICAL-BEAM PHOTOMETER

[75] Inventors: Dean G. Hafeman, Hillsborough; Calvin T. Chow, Portola Valley, both of Calif.

[73] Assignee: Molecular Devices Corporation, Sunnyvale, Calif.

[21] Appl. No.: 08/886,711

[22] Filed: Jul. 1, 1997

Related U.S. Application Data

[63] Continuation of application No. 08/506,175, Jul. 25, 1995, abandoned, which is a continuation-in-part of application No. 08/279,518, Jul. 25, 1994, abandoned.

[51] Int. Cl.[6] ............................. G01N 21/00; G01J 5/02
[52] U.S. Cl. ................ 356/440; 356/442; 356/319; 356/416; 250/339.05; 250/339.12; 250/373
[58] Field of Search ............................. 356/381–83, 51, 356/319–320, 414, 418–419, 434, 436; 250/373, 339.05, 339.12

[56] References Cited

U.S. PATENT DOCUMENTS

| | | | |
|---|---|---|---|
| 3,811,781 | 5/1974 | Lowy . | |
| 3,839,633 | 10/1974 | McKenna et al. | 250/343 |
| 3,902,812 | 9/1975 | Honkawa . | |
| 4,121,103 | 10/1978 | Calhoun | 250/343 |
| 4,498,780 | 2/1985 | Banno et al. | 356/440 |
| 4,892,409 | 1/1990 | Smith | 356/440 |
| 4,968,148 | 11/1990 | Chow et al. | 356/440 |
| 5,183,761 | 2/1993 | Freeman et al. | 436/8 |
| 5,216,488 | 6/1993 | Tuunanen et al. | 356/440 |
| 5,298,978 | 3/1994 | Curtis et al. | 356/435 |
| 5,307,144 | 4/1994 | Hiroshi et al. | 356/440 |
| 5,348,396 | 9/1994 | O'Rourke et al. | 374/161 |
| 5,440,388 | 8/1995 | Erickson | 356/349 |

FOREIGN PATENT DOCUMENTS

| | | |
|---|---|---|
| 0217632 | 4/1987 | European Pat. Off. . |
| 06039533 | 3/1985 | Japan . |
| 60-183560 | 9/1985 | Japan . |
| 61-082145 | 4/1986 | Japan . |

*Primary Examiner*—Frank G. Font
*Assistant Examiner*—Jason D. Vierra-Eisenberg
*Attorney, Agent, or Firm*—McDonnell Boehnen Hulbert & Berghoff

[57] ABSTRACT

Disclosed are photometric methods and devices for determining optical pathlength of liquid samples containing analytes dissolved or suspended in a solvent. The methods and devices rely on determining a relationship between the light absorption properties of the solvent and the optical pathlength of liquid samples containing the solvent. This relationship is used to establish the optical pathlength for samples containing an unknown concentration of analyte but having similar solvent composition. Further disclosed are methods and devices for determining the concentration of analyte in such samples where both the optical pathlength and the concentration of analyte are unknown. The methods and devices rely on separately determining, at different wavelengths of light, light absorption by the solvent and light absorption by the analyte. Light absorption by the analyte, together with the optical pathlength so determined, is used to calculate the concentration of the analyte. Devices for carrying out the methods particularly advantageously include vertical-beam photometers containing samples disposed within the wells of multi-assay plates, wherein the photometer is able to monitor light absorption of each sample at multiple wavelengths, including in the visible or UV-visible region of the spectrum, as well as in the near-infrared region of the electromagnetic spectrum. Novel photometer devices are described which automatically determine the concentration of analytes in such multi-assay plates directly without employing a standard curve.

8 Claims, 10 Drawing Sheets

DETERMINATION OF LIGHT ABSORPTION PATHLENGTH IN A VERTICAL-BEAM PHOTOMETER

This application is a continuation of application Ser. No. 08/506,175, filed Jul. 25, 1995, now abandoned which is a continuation-in-part of application Ser. No. 08/279,518 filed Jul. 25, 1994, now abandoned.

BACKGROUND OF THE INVENTION

1. Field of the Invention

This invention relates to the field of photometry. In particular, the invention relates to spectrophotometric methods and apparatus capable of determining the light absorption pathlength for various samples to be analyzed with a spectrophotometer.

2. Description of the Related Art

The problem of an undefined light absorbance pathlength in vertical-beam photometers has existed since the advent of vertical-beam photometers, i.e., for over 20 years. Substantial errors in determination of either relative optical pathlength or the concentration of analytes in vessels of unknown optical pathlength by prior art methods occur because of 1) substantial variation in solvent temperature, 2) substantial variation in solvent composition and 3) substantial presence of materials in the samples which absorb light in the wavelength region where the optical pathlength of the solvent is being monitored.

Photometry is a common measurement technique employed to monitor optical characteristics of samples. Customarily, samples contain an analyte species dissolved in a solvent at an unknown concentration. The concentration of the analyte may be determined by using a photometric device to measure the fraction of light absorbed by the sample at a specific wavelength ($\lambda$). The value of $\lambda$ is usually chosen to be near the wavelength of light where the analyte absorbs maximally. According to the Beer-Lambert law, equation 1, absorbance is determined as follows:

$$\text{Absorbance } (A_\lambda) = \log\frac{I_o}{I} = \varepsilon_\lambda \cdot l \cdot C \tag{1}$$

where $I_0$ is the incident radiation intensity, I is the intensity of light emerging from the sample, $\varepsilon_\lambda$ is the molar extinction coefficient of the analyte dissolved in the solvent, l is the light absorption pathlength, and C is the concentration of absorbing analyte in the solvent. The value of I customarily is measured with a photometric apparatus, such as a photometer or spectrophotometer, equipped with a fixed light path sample-retaining device called a cuvette, such as a 1 cm wide cuvette. The sample-retaining device contains the sample comprised of analyte dissolved in a solvent. The value of $I_0$ is ordinarily measured with the same system except that no analyte is present in the solvent. Alternatively, $I_0$ may be measured in the absence of both the sample and the sample-retaining device (this value of $I_0$ is called an "air blank"). When an "air blank" is employed, a separate $A_\lambda$ measurement of the solvent and sample-retaining device gives a "solvent blank" absorbance value. A "corrected absorbance" value related to absorbance of the analyte is then obtained by subtracting the "solvent blank" from each absorbance measurement made on the samples comprised of analyte dissolved in solvent and contained in the sample-retaining device. These two alternative procedures give mathematically equivalent results. Absorbance measurements made by either procedure allows unknown concentrations of the analyte to be determined by calculation according to Eq. 1, provided that $\varepsilon_\lambda$ and l are known.

A spectrophotometer is a photometric apparatus which employs an adjustable means to pre-select a desired portion of the electromagnetic spectrum as incident radiation. Usually spectrophotometers employ a dispersive means such as a prism or diffraction-grating monochrometer to provide continuously selectable, narrow, bands of light centered about the desired wavelength $\lambda$. Most conventional photometers and spectrophotometers employ a horizontal light beam that traverses the liquid sample horizontally so as to avoid passing through the liquid-gas interface that is typically above the sample. With such horizontal-beam photometers, the geometry and optical pathlength within the sample is fixed for any given cuvette. For visible and ultraviolet light absorption measurements, for example, cuvettes customarily have a 1 cm pathlength. Cuvettes with pathlengths between 0.1 cm and 10 cm are also common, however. With any such fixed pathlength cuvette, in a horizontal-beam photometers, unknown concentrations C of the analytes may be calculated from absorbance measurements provided that the values of $\varepsilon_\lambda$ and l are known.

When either $\varepsilon_\lambda$ and l is not known, values C of may be determined readily by employing known concentrations of the analyte dissolved in the same solvent (i.e., standards) and performing similar light-absorbance measurements on the unknowns and on the standards. The most common procedure comprises plotting $A_\lambda$ versus concentration of analyte in the standards (i.e., a "standard curve") and then comparing the results obtained with the unknown concentrations of analyte to the standard curve. This procedure provides the unknown concentrations of analyte from the "standard curve".

Vertical-beam photometers also measure light absorption in order to determine the unknown concentrations of analyte in samples. In vertical-beam, photometers, however, the light beam usually passes only through one wall of the sample-retaining device, through the sample, and through the interface between the sample a surrounding gas atmosphere (which is usually air). The latter liquid-gas interface, the meniscus, is usually curved, the specific shape depending upon the interactions between the liquid sample and the gas and the side-walls of the sample-retaining device. Depending upon the design of a particular vertical-beam photometer, the light beam may traverse the meniscus either before or after passing through the sample. In either case, the optical pathlength through the sample is not a constant value. Instead, the optical pathlength is related to the sample volume and the meniscus shape. The nature of the sample, the sample-retaining device surfaces, and gas each contributes to the shape of the meniscus, quantitatively affecting the optical pathlength through the sample. Thus, in vertical-beam photometers, the value of l in Eq. 1 usually is unknown and difficult to control reproducibly.

Vertical-beam photometry has become a popular technique despite the disadvantage of not having a fixed optical pathlength through the sample. This popularity stems from the fact that the optical characteristics of a large multiplicity of samples may be analyzed with a vertical-beam photometer in a small period of time. Typically, vertical beam photometers monitor the optical characteristics of samples disposed in the wells of, for example, 96 well multi-assay plates. The optical characteristics, such as light absorption or light scattering, of the samples contained within each well of such multi-assay plates may be monitored, typically, in 10 seconds or less. Vertical-beam photometers also allow repetitive measurements of such a multiplicity of samples to be made with intervals of 10 seconds or less between each of a series of measurements. In such a way the kinetic properties, such as the rate of change in absorbance, of a plurality of samples may be monitored in a very short time.

In vertical-beam photometry of the prior art, an approximated constant value of 1 is used for standards and unknowns. Concentrations of unknown analytes are determined, often with acceptable precision, by plotting "standard curves" using the approximated value of 1 and comparing the absorbance results obtained with unknown concentrations of analyte to the "standard curve," as mentioned previously.

The fact that a value of C may not be calculated directly from Eq. 1, but instead must be determined from a "standard curve" constructed for each analytical measurement, severely hinders the ability of vertical-beam photometric techniques. The additional time and expense required for preparing such standard curves for each analysis is often an onerous disadvantage to vertical-beam photometry. Thus, convenient, accurate, and precise methods and apparatus for determining optical pathlength of samples in vertical-beam photometers would be of great utility.

Japanese Kokai Patent Application number Sho58 [1983] - 1679Y2 discloses the unknown optical pathlength of vessels may be determined by dispensing a colored solution, with a known relationship between optical pathlength and absorbance, into the vessels and determining the absorbance of this solution. A similar method is taught in U.S. Pat. No. 5,298,978, issued Mar. 29, 1994.

Additionally Japanese Kokai Patent Application numbers Sho 60(1985]-183560 and Sho 61[1986]-82145 disclose methods of determining relative optical pathlength of aqueous samples within different reactor vessels (contained in a common reactor) by measuring the optical density of the samples at two different wavelengths in the near-infrared wavelength region from 900 to 2100 nanometers. With clear quartz reaction vessels, the reference teaches that $(A_{975}-A_{900})$, $A_{1195}-A_{1070})$, or $(A_{1260}-A_{1070})$ may be used to determine the relative optical pathlength through aqueous samples. For reactors made of synthetic acryl resins, where the resin has interfering absorption bands, the prior art teaches that $(A_{970}-A_{1070})$ or $(A_{1280}-A_{1070})$ may be used to determine relative optical pathlength of the samples. Once relative optical pathlength is known for each of the vessels of the reactor, then optical density values of an analyte (measured at a third wavelength) may be normalized for variation in optical pathlength to obtain the relative concentration of analyte in each reactor vessel. Employing vessels with known concentrations of analyte allows on to determine the absolute concentrations of analyte within other vessels.

There also exists need for methods and apparatus that may be utilized with samples that are dissolved in a variety of different solvents or in mixtures of different solvents. Because analytes are extremely diverse and may have diverse light-absorption properties, there exist no apparatus capable of determining concentration and optical pathlength of any analyte dissolved in various solvents or mixtures of solvents. Further complicating this situation is the extreme variability of concentrations of analytes from one sample to the next.

SUMMARY OF THE INVENTION

The instant invention provides a solution to the problem of undefined light absorbance pathlength in vertical-beam photometers. The invention provides methods and devices that are convenient to employ and that require minimal additional measurement apparatus. Thus, the cost associated with making such measurements is kept to a minimum.

The invention further provides methods and apparatus for determining optical pathlength and sample concentration that furnish accurate and reproducible results. The results, determined by using the invention in vertical-beam photometers, are essentially interchangeable and indistinguishable from those obtained in horizontal-beam photometry.

The invention also provides methods and apparatus for determining optical pathlengths between 1 millimeter and 1 centimeter in aqueous samples within vertical-beam photometers. The inventive methods and apparatus may be utilized with samples that are dissolved in a variety of different solvents or in mixtures of different solvents.

Thus, in one embodiment of the invention, optical pathlength is determined in vertical-beam photometers by analyzing an optical property of the sample solvent which is dependent upon optical pathlength but independent of all relevant concentrations of all analytes which may possibly be contained within a sample solvent.

The invention provides vertical-beam photometric devices comprising:

a means for detecting light signals transmitted through a first liquid sample and a second liquid sample, the first and second samples comprised of at least a liquid solvent and being contained in sample-containing means of known optical pathlength;

a means for determining the difference in absorbance of the liquid samples at two different wavelengths of light;

a means for detecting light transmitted vertically through a third liquid sample disposed in a sample assay plate where the third liquid sample is comprised of an analyte dissolved or suspended in the solvent and having an unknown optical pathlength and an unknown relationship between light absorbance of the analyte and the optical pathlength; and a means for determining the light absorption pathlength for the third liquid sample by relating the differences in light transmitted through the first and second samples, at the two different wavelengths to the amount of light transmitted through the third sample.

The invention also encompasses vertical-beam photometric devices for measuring the rate of change in optical characteristics of samples contained in sample sites disposed on an assay plate, the device comprising:

a wavelength selection means for selecting a first wavelength band of light from a first wavelength range and for selecting a second and a third wavelength bands of light from within a second wavelength range;

a sample-retaining means for retaining one, or more, samples, and a light-transmitting means for transmitting the light from the light source to the wavelength selection means and through the one, or more, samples;

a photodetector means for detecting the first, second and third bands of light transmitted through a selected sample, and for providing a first, a second and a third signal in respective relationship to the first, second and third bands of light so transmitted;

a means for determining the optical pathlength of the first band of light transmitted through the selected sample from the difference of the second and third signals; and a means for relating the first signal to the optical pathlength so determined so as to determine and automatically indicate optical parameters including either the absorbance or the fraction of incident light transmitted through the selected sample per unit optical pathlength of the selected sample.

and additionally a means for kinetic analysis of the signal of the photodetector means relating to the selected site so as to determine the rate of change of the optical parameters.

DESCRIPTION OF THE PREFERRED EMBODIMENTS

Figure 1:
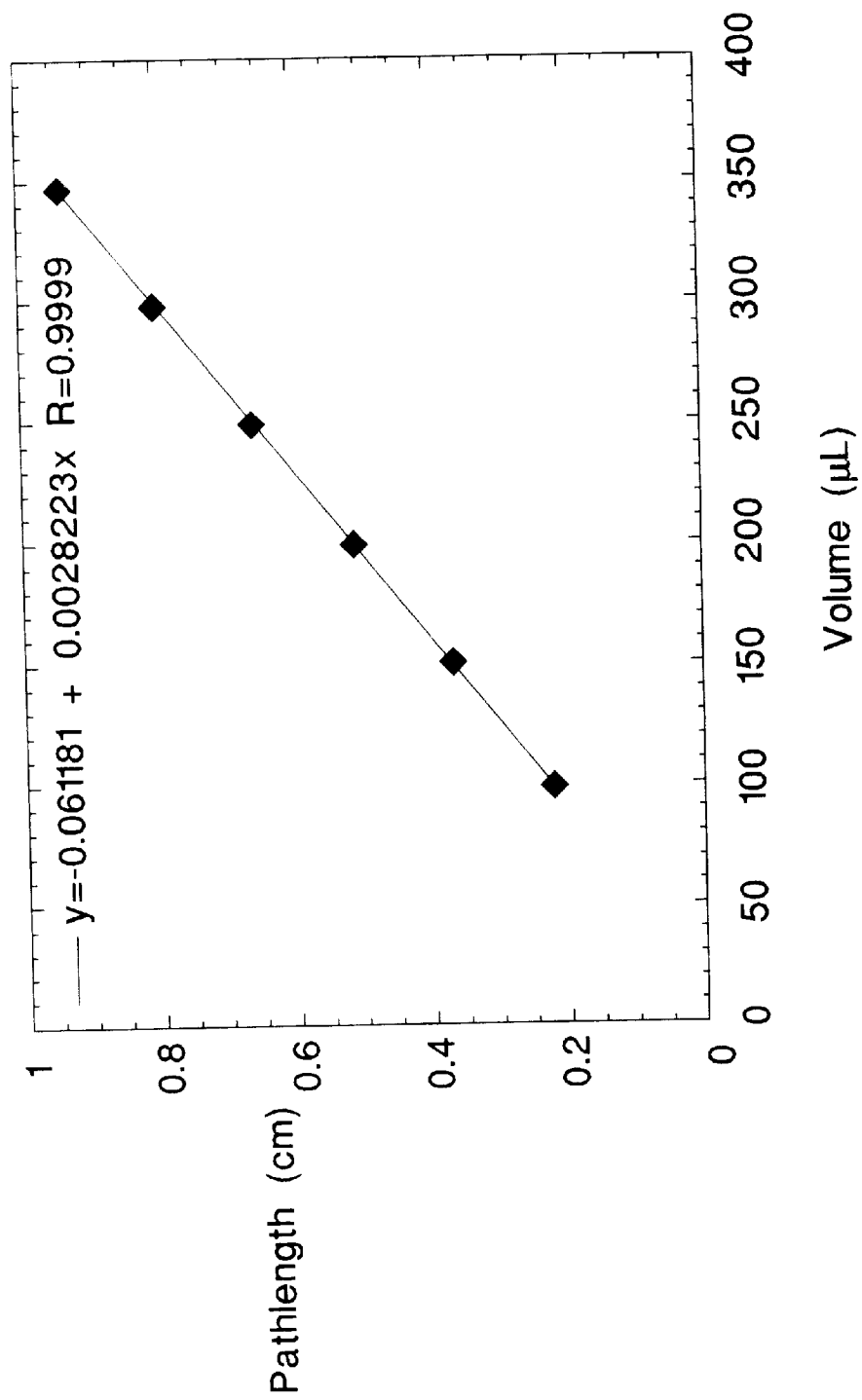
FIG. 1 is a graph showing calibration of pathlength versus volume in a NUNC 96-well microplate.

As used herein, A indicates an absorbance value measured according to Eq. 1 and a subscripted value following A indicates the center of the bandpass spectrum of light (given in nanometers) that is used to make the light-absorbance measurement. For example, $(A_{1770}-A_{1310})$ is the mathematical difference between absorbance measurements, made on the same sample with the same optical pathlength, with 1770 nanometer and 1310 nanometer center bandpass incident light respectively. In certain situations the fraction of incident light transmitted $(I/I_0)$ may be employed rather than the amount of light absorbance ($\log I_0/I$) after accounting for the mathematical relationship between these two parameters.

The solvents suitable for use in the invention and apparatus of the invention may be any solvent although those absorbing light in the near-infrared region are preferred. Particularly preferred solvents are those having low ultraviolet and visible absorbance spectra. Such solvents are those typically having low electronic transition properties at energy levels corresponding to light of 108 to 750 nanometer wavelength. For electronic transition probabilities of various solvents, see "High Purity Solvent Guide," James T. Przybytek, ed., 1992, Burdick & Jackson Laboratories, Inc., Muskegon, Mich.

As used herein, the near-infrared portion of the electromagnetic spectrum is that portion extending from about 750 to 2500 nanometers (i.e., from about 0.750–2.5 microns wavelength or, in wavenumbers, about 13,300–4000 $cm^{-1}$). Liquid water absorbs light with values of $\epsilon_\lambda \cdot C$ between 0.01 and 60 $cm^{-1}$ within the near infrared region. At room temperature, the values of $\epsilon_\lambda \cdot C$ for pure water is about 0.18 $cm^{-1}$ near 970 nanometers and is about 0.58 $cm^{-1}$ near 1200 nanometers wavelength. These values may be found in Luck, *Berichte der Bunsengesellschaft* 67: 186–189, 1963; and Thomas et al., *The Journal of Physical Chemistry*, 69: 3722–3726, 1965.

The light absorbance pathlength customarily employed in vertical-beam photometry is between 1 millimeter and 1 centimeter.

According to Eq. 1, the values of $A_\lambda$ at wavelengths of about 970 nanometers and about 1200 nanometers are 0.018 or 0.058, respectively, for a 1 millimeter light absorption pathlength and 0.18 or 0.58, respectively, for a pathlength of 1 centimeter in pure water at room temperature. These values are well within the range of 0.01 to 4.0 absorbance units which is generally desirable for precise optical density measurements in vertical-beam photometers.

It has been unexpectedly discovered that near-infrared analysis of water at selected wavelengths is sufficiently robust to give an accuracy of less than 5% variation from the true pathlength value in vertical-beam photometry. This discovery is surprising since: (1) absorption of light by molecules in the near-infrared region (NIR) of the electromagnetic spectrum is due to overtones or combinations of overtones originating from fundamental absorption bands in the mid-infrared region extending from 4000 to 600 $cm^{-1}$; (2) absorbance in the mid-infrared region is due to intramolecular bond stretching and bending vibrational motions and is highly dependent upon the extent of hydrogen bonding in aqueous solutions; and (3) physical parameters such as temperature or ionic strength, for example, influences the absorption coefficient and wavelength of maximum absorbance. In addition, analytes present in water may potentially influence hydrogen bonding within the solvent, thus changing the absorption properties of the water solvent. These problems are discussed in the *Handbook of Near-Infrared Analysis*, Donald A. Burns, Emil W. Ciurczak, eds., Marcel Dekker, Inc., 1992. See also, G. L. Kemeny and D. L. Wetzel, "Moisture: Study of a Lively Near-Infrared Diffuse Reflectance Spectrum," Paper 117, FACSS 13th Annual Meeting, Sept. 28–Oct. 3, 1986, St Louis, Mo.; and G. J. Kemeny and D. L. Wetzel, "Differences in the Spectrum of Water," AACC Annual Meeting, Nov. 1–6, 1987, Nashville, Tenn. Furthermore, vertical-beam photometry samples customarily have a curved meniscus and no single unique pathlength exists for all rays of light passing through the sample.

The methods and apparatus of the invention may be used to determine various light absorption pathlengths within vertical-beam photometers containing samples, preferably light absorption pathlengths between about 1 millimeter and 1 centimeter. Further, the invention may be used with a variety of solvents and analytes. Disclosed herein are four embodiments suitable for determining light absorption pathlengths. These methods each utilize measurement of absorbance of the sample solvent in the near-infrared region of the electromagnetic spectrum (NIR).

The first embodiment is especially well suited for use in determining optical pathlength in purely aqueous solvents within a moderate temperature range. This embodiment may be used at temperatures from about room temperature to the temperature of the human body (i.e., from about 20 to 40° C.).

The second embodiment may be used to determine light absorption pathlength with samples in aqueous solvents over a broader range of temperatures, i.e., from about 0 to 100° C.

The third embodiment is suitable for determining light absorption pathlength in mixtures of aqueous and non-aqueous solvents.

Finally, the fourth embodiment is preferred for use with nonaqueous solvents having values of $\epsilon_\lambda \cdot C$ of from about 0.05 and 5 cm$^{-1}$ within the near infrared to infrared regions of the electromagnetic spectrum from about 800 to 6000 nanometers.

All documents, e.g., patents and journal articles, cited above or below are hereby incorporated by reference in their entirety.

Vertical-beam photometers suitable for carrying out the invention will have the following:

1. a light source, such as a tungsten-halogen, xenon flash lamp, mercury arc lamp, or the like;
2. a wavelength selection means capable of selecting bands of light in the ultraviolet-visible region of the electromagnetic spectrum from between 100 to 750 nanometers. (These ultraviolet-visible bands will normally be used for analysis of concentration of analytes in samples comprised of at least one analyte dissolved in a solvent);
3. a wavelength selection means capable of selecting bands of light in the infrared region of the electromagnetic spectrum greater than 750 nanometers;
4. a light-distribution means, such as optical lenses and mirrors for directing light, or a system of fiber optics for directing the light;
5. a sample-retaining means for retaining samples disposed on a multi-assay plate, such as the NUNC 96-well microplate; and
6. a light detection means, such as photo-diodes, photo-conduction cells, a photo-multiplier, photo-Darlington cells, a diode-array, or the like capable of detecting both the bands of the light in the ultraviolet visible region and the bands of light in the infrared region;
7. a means for determining the optical pathlength of the samples, as described above. Suitable wavelength selection means for both the ultraviolet-visible region and the infrared region of the electromagnetic spectrum include optical filters of colored glass, or the like, interference filters, or monochromators for dispersing the light and selecting a band of light. With either filters or a monochrometer the bands of light, desirable will be narrow, in the range of 1 to 25 nanometers bandwidth. Preferably the bands will be even narrower, but not so narrow as to unduly limit the amount of light provided, generally in the 5–10 nanometer range. Usually the wavelength selection means capable of selecting bands of light in the infrared region will need to select bands of light only in the near-infra-red region of the electromagnetic spectrum from 750 nanometers to 2500 nanometers wavelength. Alternatively, a laser, such as a helium-neon, argon ion, carbon dioxide, or solid state laser, e.g. a GaAlAs laser, could be used to fulfill both the requirement for a light source and a wavelength selection means. When more than on band of wavelengths is desired, two, or more, lasers or light-emitting diodes may be combined as the light source and the desired wavelength range may be supplied by turning on the light source emitting the desired wavelength band of light. Such lasers have the advantage of having high light intensity at extremely narrow bandwidth. Alternatively, light-emitting diodes (LEDs) may be used to supply light of the desired wavelength range. A variety of LEDs may be used selectively to provide the desired wavelength bands of light when switched from on to off. Alternatively, the LEDs or laser sources of light may be used in conjunction with a white light source, together with optical filters or a monochrometer. In this way, the wavelength range and intensity of the white light source may be extended at a desired wavelength.

A vertical-beam photometer suitable for monitoring the absorbance of liquid samples in the ultraviolet-visible and the near-infrared portions of the electromagnetic spectrum when fitted with the appropriate interference filters, is described in U.S. Pat. Nos. 4,968,148 and 5,112,134. A vertical-beam photometer disclosed in pending U.S. patent application Ser. No. 08/228,436 (Case No. 93,1127) also would be suitable when fitted with a monochrometer capable of providing bands of light in the near-infrared portion of the electromagnetic spectrum. Such a monochromater is Part No. 36-0504 available from Optometrics Inc., Ayer, Mass.

One skilled in the art will recognize that modifications may be made in the present invention without deviating from the spirit or scope of the invention. The invention is illustrated further by the following examples which are not to be construed as limiting the invention or scope of the specific procedures described herein.

Experimental Measurements:

a.) Instrumentation:

A Thermomax™ microplate reader, commercially available from Molecular Devices Corporation, Menlo Park Calif., USA, is used to make all vertical-beam photometry measurements. Nominally 900 and 970 nanometer interference optical filters may be obtained from Andover Corporation, Salem, N.H. The nominally 900 nanometer filter (Cat. No. 900FS10-25) is centered at 902.6 nanometers with 11.5 nanometer bandwidth at half maximal transmittance. The nominally 970 nanometer filter (Cat. No. 970FS10-25) is centered at 970.0 nanometers and has a 8.5 nanometer bandwidth at half maximal transmittance. Other optical filters were obtained as catalog items from Molecular Devices Corporation. Horizontal-beam photometric measurements, made for comparative purposes, are made in a Hewlett-Packard Model 8451A diode array spectrophotometer equipped with a 1 cm light path cuvette.

b.) Reagents:

The following reagents may be obtained from Aldrich Chemical Co., Milwaukee, Wis.: Acid Orange 8 (Cat. No. 21,453-1), Acid Orange 74 (Cat. No. 20,181-2), Azure B (Cat. No. 86,105-7), Direct Yellow 62 (Cat. No. 20,206-1), Naphthal Green B (Cat. No. 11,991-1). Bromocresol Purple was obtained from Sigma Chemical Co. (Cat. No. B-4263). The spectra of these compounds in the ultraviolet and visible regions of the electromagnetic spectrum is given in, *The Sigma-Aldrich Handbook of Stains, Dyes and Indicators*, by Floyd J. Green, 1990© Aldrich Chemical Co., Inc., Milwaukee, Wis. Durkee Yellow Food Color may be obtained from Durkee Famous Foods SCM Corporation, Westlake, Ohio. Schilling Blue Food Color was obtained from McCormick & Co., Inc., P.O. Box 208, Hunt Valley, Md. Obtainable from Sigma Chemical Co. is PIPES (Piperazine-N,N'-bis[2-ethanesulfonic acid]), sodium salt, Cat. No. P-6757.

c.) Multi-Assay Plates:

For vertical-beam photometry, samples are contained within wells of a 96-well microplate multi-assay plate. The microplates are Nunclon® Delta 96-well, flat-bottom plates which may be obtained from VWR Scientific, Brisbane, Calif.

d.) Experimental Conditions:

All measurements were made at room temperatures between 20 and 25 degrees centigrade.

EXAMPLE 1

In this example a vertical-beam photometer was also used as a horizontal-beam photometer. For these measurements, a 1.00 cm pathlength quartz cuvette is filled with pure de-ionized water and capped with a Teflon® stopper which is taped to the cuvette. The capped cuvette was placed horizontally in a vertical-beam photometer so that a selected band of incident light is passed through one clear (transparent) wall of the cuvette, next through the pure water sample, and finally through the opposite clear (transparent) wall of the cuvette before being measured by the photodetector of the photometer. The results of such measurements are equivalent to measurements made by horizontal-beam photometry. The band of incident light is first selected by passing through either the nominally 900 nanometer center-band or the 970 nanometer center-band interference filter (each of which have approximately a 10 nanometer wide bandwidth at half-maximal intensity). The resulting photometric values were used as I. Values of $I_0$ for each optical filter were obtained with neither the water sample nor the cuvette in the incident light path (air blank). Absorbance values are calculated by the photometer at each pre-selected wavelength by using Eq. 1. The difference in absorbance values of the 1.00 cm optical pathlength cuvette filled with pure water measured with the nominally 970 nanometer center-band filter used to provide incident light and the 900 nanometer center-band filter used to provide incident light (i.e. $A_{970}-A_{900}$) was found to be 0.180.

Next, similar measurements of $A_{970}-A_{900}$ were performed on six different samples containing chromophoric analytes. These values are referred to as Sample $A_{970}-A_{900}$. Prior to measurement, the analytes were dissolved in the de-ionized water at concentrations sufficient to yield samples having absorbance values of between 1.0 and 3.0 absorbance units at their respective maximal light absorption wavelengths in the visible spectral region when placed in the same 1 cm optical pathlength cuvette. The analytes are Acid Orange 8, Acid Orange 74, Azure B, Direct Yellow 62, Durkee Yellow Food Color, and Schilling Blue Food Color. The values of $A_{970}-A_{900}$ obtained experimentally range from 0.180 to 0.183. A similar measurement for another sample comprising Bromocresol Purple as an analyte in a solvent mixture of 12 mM PIPES (Piperazine-N,N'-bis[2-ethanesulfonic acid]) and 38 mM Sodium Phosphate Buffer (1.0 parts 0.05 M PIPES: 3.14 parts 0.05 M Sodium Phosphate Buffer by volume, final pH=5.8), similarly was found to be 0.183. From Eq. 1, the value of $(A_{970}-A_{900})\cdot C$ for these aqueous samples at room temperature, is about 0.182 $cm^{-1}\pm 0.002$ $cm^{-1}$. Based upon this result, values of $(A_{970}-A_{900})\cdot C$ within this range, predictably might be employed generally to calculate light absorption pathlength from measured values of $A_{970}-A_{900}$ for a variety of aqueous samples at room temperature. According to this prediction obtained from a small number of experimental samples, light absorption pathlength may be determined for aqueous samples at temperatures ranging from about 15 to 40° C., preferably about 23° C., according to Eq. 2 with less than about 5% error as follows:

$$\text{Light Absorption Pathlength} = \frac{A_{970} - A_{900}}{0.182 \text{ cm}^{-1}} \quad (2)$$

Absorbance of samples per unit pathlength may be found by measuring the absorbance, $A_x$, of samples at a preselected wavelength, x, preferably near the absorbance maximum of the analyte. The resulting values are referred to as Sample $A_x$. Light Absorbance per unit Pathlength in aqueous samples is calculated using equation 3, as follows:

$$\text{Light Absorbance per Unit Pathlength} = \frac{\text{Sample } A_x(0.182 \text{ cm}^{-1})}{\text{Sample } A_{970} - A_{900}} \quad (3)$$

From these results and the temperature data provided in Berichte der Bunsengesellschaft, supra, even greater precision may be obtained by a) measuring the temperature of the sample, or alternatively of the sample compartment enclosing the aqueous sample, and b) adjusting the denominator of the right side of Eq. 2 and Eq. 3 for the estimated temperature of the sample. For example, for aqueous samples at 2° C., the adjusted denominator on the right side of Eq. 2 would be about 0.157 $cm^{-1}$, for 10° C. about 0.168 $cm^{-1}$, for 20° C. about 0.180 $cm^{-1}$, for 30° C. about 0.190 $cm^{-1}$, for 40° C. about 0.200 $cm^{-1}$, for 50° C. about 0.210 $cm^{-1}$, for 60° C. about 0.220 $cm^{-1}$, for 70° C. about 0.230 $cm^{-1}$, for 80° C. about 0.240 $cm^{-1}$, and for 90° C. about 0.250 $cm^{-1}$. Intermediate values of $(A_{970}-A_{900})\cdot C$ for intermediate temperatures may be obtained by interpolation.

In this example, the cuvette was placed horizontally in the light beam without the use of any fixed retaining means. These horizontal-beam photometric measurements made at the individual 970 and 900 nanometer wavelengths varied by as much as ±0.050 absorbance units from measurement to measurement. The differential $A_{970}-A_{900}$ values, however varied, by no more than ±0.002 absorbance units. Thus, the $A_{970}-A_{900}$ value is relatively independent of the angle of the incident test light with respect to the sample cuvette in horizontal-beam photometry. Differential measurements, such as the $A_{970}-A_{900}$ value, therefore function to eliminate errors due to variation of cuvette angle with respect to the beam of test light in horizontal-beam photometry. Alternatively a fixed sample-retaining means would also help to reduce such errors.

Next the same sample solutions were dispensed into the wells of a 96-well microplate at sample volumes of 350, 300, 250, 200, 150, or 100 μl per well. Each sample composition and volume combination was tested in 8 replicate wells of the microplate. Absorbance values for each well within the microplate, with incident light passing substantially vertically through the wells, were measured in the vertical-beam photometer at the same center-band wavelengths employed for the respective samples in the horizontal-beam spectrophotometer measurements, as well as at 970 and 900 nanometers center-band wavelengths. "Solvent blank," absorbance values of the pure water solvent were also measured in the vertical-beam vs. an "air blank" at each measurement wavelength. The appropriate "solvent blank" at each center-band wavelength of incident light is subtracted from the experimental absorbance measurements, which employed "air blank" values of $I_0$ according to Eq. 1 above. These individual, "solvent blank"-corrected absorbance values are determined for each analyte near its wavelength of maximal absorbance in each well of the microplate. Also, the optical pathlength (i.e. the light absorption pathlength) is calculated from $A_{970}$–$A_{900}$ data obtained from each well in the microplate according to Eq. 2 above. The individual, "solvent blank"-corrected absorbance values determined for each analyte near its wavelength of maximal absorbance are then divided by the optical pathlength for each well of the microplate. These values are termed specific absorbance values. The specific absorbance values of each analyte (i.e, the absorbance per unit pathlength, reported in units of $cm^{-1}$) are shown in Table I, below.

For example, the concentration of water in one (1) molar sodium chloride aqueous solution, at 0° C., is about 55.6, substantially the same as for pure water at the same temperature. Thus, any optical property of water that is dependent upon the light absorption pathlength within the water, as well as the water concentration, may be used to monitor the optical pathlength within aqueous samples containing analytes, provided that the optical property is otherwise unaffected by such analytes.

It is preferred, in most aqueous samples, to maintain a high concentration of the water solvent relative to the concentration of the dissolved analytes.

TABLE I

Optical Density/Cm Pathlength Measured In
A Vertical-Beam Photometer vs. A Spectrophotometer

| Chromophore (wavelength) | Absorbance per Centimeter Pathlength [A/cm ($cm^{-1}$)] Microplate Volume | | | | | | A/cm Microplate 150–350 µl Mean ± S.D ($cm^{-1}$) (CV in %) | A/cm Horitontal-Beam Spectrophotometer ($cm^{-1}$) | Microplate vs. spectrophotometer Difference ($cm^{-1}$); (% diff.) |
|---|---|---|---|---|---|---|---|---|---|
| | 350 µl | 300 µl | 250 µl | 200 µl | 150 µl | 100 µl | | | |
| Acid Orange 8 (490 nm) | 2.37 | 2.33 | 2.32 | 2.33 | 2.34 | 2.37 | 2.34 ± 0.019 CV = 0.00% | 2.28 | 0.06 (2.5%) |
| Acid Orange 74 (480 nm) | 1.59 | 1.59 | 1.59 | 1.59 | 1.59 | 1.61 | 1.59 ± 0.000 CV = 0.00% | 1.54 | 0.05 (3.2%) |
| Azure B (650 nm) | 1.43 | 1.44 | 1.44 | 1.46 | 1.45 | 1.47 | 1.44 ± 0.011 CV = 0.76% | 1.46 | 0.02 (1.0%) |
| Blue Food Color (630 nm) | 1.67 | 1.67 | 1.67 | 1.67 | 1.66 | 1.68 | 1.67 ± 0.004 CV = 0.24% | 1.66 | 0.01 (0.6%) |
| Bromocresol Purple (420 nm) | 1.15 | 1.15 | 1.17 | 1.16 | 1.16 | 1.18 | 1.155 ± 0.008 CV = 0.52% | 1.10 | 0.05 (4.8%) |
| Bromocresol Purple (590 nm) | 0.996 | 0.992 | 1.008 | 0.999 | 1.001 | 1.019 | 0.999 ± 0.006 CV = 0.60% | 0.955 | 0.04 (4.6%) |
| Direct Yellow 62 (340 nm) | 1.70 | 1.70 | 1.70 | 1.70 | 1.73 | 1.76 | 1.71 ± 0.013 CV = 0.76% | 1.70 | 0.01 (0.4%) |
| Yellow Food Color (420 nm) | 2.67 | 2.62 | 2.59 | 2.59 | 2.59 | 2.61 | 2.61 ± 0.019 CV = 0.73% | 2.62 | 0.01 (0.3%) |

As shown in Table I, the coefficient of variation (CV) variation for the measurement of specific absorbance values, made at the five greatest sample volumes for each of the seven different analytes made at eight different wavelengths, was less than 1%. Further, even lowest volume (100 µl) samples yielded acceptable specific absorbance results. The CV of the specific absorbance measurements for the 100 µl samples, however, slightly exceeded 1%. The reason for this increase in CV at the lowest volume (100 µl) is that optimal precision in vertical-beam photometers requires an optical density of 0.100, or greater. As shown in FIG. 1, in a typical 96-well microplate, a 100 µl volume only gives about 0.2 cm optical (light absorption) pathlength. Employing the relationship shown in equation 2 above, we see that a 100 µl aqueous volume in these microplates will produce only about 0.036 absorbance units in $A_{970}$–$A_{900}$, which is substantially less than the 0.100 required for optimal precision.

Because there is diminished precision with such small sample volumes (between 10 and 100 µl) for example, in preferred embodiments, precision of better than 1% may be obtained in determination of light absorption pathlength by averaging multiple measurements of $A_{970}$–$A_{900}$.

Absorbance values measured in a horizontal-beam spectrophotometer with identical sample solutions in a 1 cm light path cuvette are similar to those obtained with the vertical-beam photometer, after correcting for the determined optical (light absorption) pathlength.

Particularly preferred results are obtained when the concentration of solvent is relatively unchanged by the analyte.

It is further preferred that absorbance measurements of the aqueous solvent not be made exactly at the wavelength of maximal absorbance of the water. Instead, absorbance measurements are preferably made at a center-band wavelength selected to be between a local maximum and a local "pseudo-isosbestic point" in absorbance of the solvent in the NIR. Such "pseudo isosbestic" wavelengths exist for light absorbance by solvents such as water.

In general, the wavelength where two absorbing chemical species in equilibrium have identical absorptive optical properties is called an isobestic point. The existence of an isobestic point is often taken as evidence for the existence of two inter-convertible absorbing forms of a species having overlapping absorption spectra. For example, the spectra of simple pH indicator dyes, (e.g. Phenol Red) show isobestic points as a function of pH. Phenol red, for example, has an isobestic point at 495 nanometers, where the protonated form absorbs optimally close to 420 nanometers, and unprotonated form of the dye absorbs maximally at 560 nanometers wavelength. The equilibrium between the protonated and unprotonated forms of the dye shifts as a function of temperature due to a non-zero ionization enthalpy of the dye. An isobestic point of Phenol Red is observed as a function of temperature because the fundamental light-absorptive properties of both the unprotonated and protonated forms of the dye are substantially unaffected by temperature variation.

In contrast, when two inter-convertible absorbing forms of a species with overlapping spectra exist but the measured optical property of at least one of the individual chemical species is affected by a variable, the "perfect" isosbestic is destroyed. For example spectral narrowing or broadening of an individual chemical species with temperature variation will result in such a phenomenon. If the variation from a perfect isosbestic is slight, a "pseudo-isosbestic" is said to exist. Such pseudo-isosbestic points are, in fact, observed in the near-infrared absorptive properties of water, as a function of both temperature and ionic strength variation.

At these "pseudo isosbestic" wavelengths the absorbance values are nearly unaffected by temperature or hydrogen-bonding influences. Water, for example, has multiple "pseudo isosbestic" wavelengths, with respect to temperature variations, which occur between about 980–1010 nanometers, again near 1080–1120 nanometers, again near 1180–1200 nanometers, again near 1280–1320 nanometers, again near 1440–1460 nanometers, and again near 1750–1800 nanometers. Therefore, when the optical pathlength for aqueous samples is determined from NIR absorbance measurements in these spectral regions, the variation in the results due to temperature and hydrogen-bonding variations from sample-to-sample, is minimized. It is further preferred that the following absorbance differences for water, $(A_{1000}-A_{900})$, $(A_{1185}-A_{1100})$, $(A_{1440}-A_{1310})$, or $(A_{1770}-A_{1310})$ will be measured in order to determine the optical pathlength of aqueous samples.

The embodiment demonstrated in this example utilizes the absorbance difference $A_{970}-A_{900}$, rather than any one of the above parameters, employing exactly the "pseudo isosbestic" wavelengths, because the $A_{970}-A_{900}$ values are preferred NIR wavelengths for measuring absorbance with the silicon photodetectors present in the Thermomax™ microplate reader employed for the measurements. Since silicon photodetectors do not provide reasonable detectivity at wavelengths substantially greater than 1100 nanometers, the 970 nanometer wavelength was selected as the wavelength of choice to monitor the absorbance of water to obtain suitable absorbance values at the preselected wavelength with samples as small as 150 $\mu l$ and to ensure that the CV of the measurements would be less than 1%. Alternatively, greater precision and less sensitivity to temperature and sample variations can be obtained by providing vertical-beam photometers with light detectors having good detectivity in the NIR region longer than 1100 nanometers wavelength. Suitable detectors include, for example, thermal-type detectors, such as thermocouples, thermistor or pneumatic devices. Alternatively NIR semiconductor photodetectors, such as InGaAs, PbS, InAs, or Ge detectors, could be used. With these photo-detectors, any of the above disclosed "pseudo-isobestic pairs," $(A_{1000}-A_{900})$, $(A_{1185}-A_{1100})$, $(A_{1440}-A_{1310})$, or $(A_{1770}-A_{1310})$, could be used directly to monitor the light absorbance pathlength of water. With such alternative photodetectors, the $(A_{1185}-A_{1100})$ pair is most optimal because the absorbance of water at 1185 nanometers is about 0.545 cm$^{-1}$, which is very nearly optimal for maximum signal-to-noise ratios in vertical-beam photometers employing light-absorbance pathlengths of from 0.2 cm to 1.0 cm.

EXAMPLE 2

The method described in this example allows measurements of optical pathlength with mixtures of aqueous and nonaqueous solvents. It also provides for correction when substances, other than water, that may absorb at the NIR wavelengths selected to monitor optical pathlength in vertical-beam photometry are present in the solvent. In this example, the NIR wavelength difference, A970–A900, is used to monitor pathlength in aqueous samples. Alternatively, the "pseudo-isobestic pairs," described above provide superior results under certain conditions. For example, the $(A_{1000}-A_{900})$ pair will provide superior results with silicon photodetectors when the light absorption pathlength is in excess of about 0.4 cm. because in this case an absorbance value of about 0.060 will be obtained. The $(A_{1185}-A_{1100})$ pair will provide superior results when a vertical-beam photometer is used which employs photodetectors sensitive to light at wavelengths of 1100 and 1185 nanometers in the NIR because even larger absorbance values may be obtained with even smaller light absorbance pathlengths. This method is as follows:

1. Load the solvent employed to dissolve the analyte into a cuvette of known optical pathlength, for example, a 1 cm optical pathlength cuvette. This pathlength is known as the Solvent Pathlength. Place the cuvette in a photometer and measure $A_{970}-A_{900}$. This parameter is referred to as Solvent $A_{970}-A_{900}$. (The cuvette may be stoppered and placed on its side in the incident light path of vertical-beam photometers in order to accomplish this step).

2. Repeat part 1 in the same known optical pathlength cuvette, now with the analyte of interest in the solvent. The resulting parameter is referred to as Reference $A_{970}-A_{900}$. Also measure, approximately, the absorbance, $A_x$, of the analyte at the wavelength which will be used for subsequent measurements of analyte concentration. This parameter is referred to as Reference $A_x$. Preferably, the absorbance of the analyte is estimated to be a value between 1.0 and 2.0).

3. Measure the values of $A_x$ in samples with the vertical-beam photometer as is customary. These parameters are referred to as Sample $A_x$. Also measure $A_{970}-A_{900}$ values of the sample samples with the vertical-beam photometer. The later parameter is referred to as Sample $A_{970}-A_{900}$. The light absorption pathlength in each of the samples is determined using equation 4 as follows:

$$\text{Light Absorption Pathlength} = \frac{\text{Sample } A_{970} - A_{900} - \left\{ \frac{\text{Sample } A_x}{\text{Reference } A_x} [(\text{Reference } A_{970} - A_{900}) - (\text{Solvent } A_{970} - A_9)}{\text{Solvent } A_{970} - A_{900}} \right.}{\text{Solvent Pathlength}} \quad (4)$$

Light Absorbance per unit Pathlength for the samples is determined from equation 5 as:

Light Absorbance per unit Pathlength = (5)

$$\frac{(\text{Sample } A_x)(\text{Sample } A_{970} - A_{900})}{\text{Solvent Pathlength}}$$

$$\text{Sample } A_{970} - A_{900} - \left\{\frac{\text{Sample } A_x}{\text{Reference } A_x}[(\text{Reference } A_{970} - A_{900}) - (\text{Solvent } A_{970} - A_9)\right.$$

Preferably, the means for determining optical pathlength and automatically determining and indicating light absorbance per unit pathlength (i.e., specific absorbance) are included in a vertical-beam photometric device capable of monitoring the optical density of samples contained in a multi-assay plate at a minimum of three (3) different center-band wavelengths of incident light. The device preferably will include means for determining and indicating if the analyte presents significant interference with a simple, uncorrected, determination of Optical Pathlength. An Interference Parameter is determined from equation 6 as follows:

greater than the results obtained in the spectrophotometer by 101% (i.e. more than 2-fold greater). Eq. 5, however, provides results from the vertical-beam measurements with the vertical-beam photometer that are substantially identical to those from the horizontal-beam spectrophotometer.

Interference Parameter = (6)

$$\frac{\text{Sample } A_{970} - A_{900} - \left\{\frac{\text{Sample } A_x}{\text{Reference } A_x}[(\text{Reference } A_{970} - A_{900}) - (\text{Solvent } A_{970} - A_9)\right.}{\text{Solvent } A_{970} - A_{900}}$$

Significant interference is deemed to be absent when the Interference Parameter given by Eq. 6 is between 0.95 and

TABLE II

Light Absorbance/Cm Pathlength of an Interfering Analyte Determined with and without Correction for the Optical Interference of Napthal Green B

| Naphthal Green B | Absorbance per Centimeter Pathlength i.e. A/cm (cm$^{-1}$) Microplate Volume | | | | | | A/cm Microplate 150–350 μl Mean ± S.D. (cm$^{-1}$) | A/cm Horitontal-Beam Spectrophotometer | Microplate vs. Spectrophotometer difference (cm$^{-1}$) |
|---|---|---|---|---|---|---|---|---|---|
| (725 nm) | 350 μl | 300 μl | 250 μl | 200 μl | 150 μl | 100 μl | (CV in %) | (cm$^{-1}$) | (% diff.) |
| Uncorrected A/cm (Eq. 3) | 2.40 | 2.39 | 2.40 | 2.41 | 2.44 | 2.51 | 2.41 ± 0.019 CV = 0.08% | 1.2 | 1.21 + 101% |
| corrected A/cm (Eq. 5) | 1.21 | 1.20 | 1.21 | 1.21 | 1.22 | 1.23 | 1.21 ± 0.007 CV = 0.06% | 1.20 | 0.01 + .8% |

1.05 for example. Thus, the interference of the analyte creates less than a 5% error in determination of Optical Pathlength. The device preferably will include automatic means for determining and indicating when any of the parameters Sample $A_x$, Sample $A_{970}$–$A_{900}$, Reference $A_x$, Reference $A_{970}$–$A_{900}$, or Solvent $A_{970}$–$A_{900}$ are less than 0.05 and, thus, too low to provide an accurate estimation of interference.

Shown in Table II are the measurements of absorbance of Napthal Green B in aqueous solvent samples determined according to the method set forth in this example above. For comparison purposes the results are determined according to Eq. (3) and according to Eq. (5). The Light Absorbance per unit Pathlength measurements made according to Eq. (3) in the vertical-beam photometer (microplate reader) were The procedure described in this example also allows Light Absorption Pathlength and Light Absorbance per unit Pathlength to be determined for mixtures of aqueous and non-aqueous solvents. Such mixtures may include, for example, water, methanol, ethanol, propanol, acetone, acetonitrile, pyridine, glycerol, tetrahydrofuran, di- and trichlorobenzenes, or derivatives thereof, and organic esters such as methyl- or ethyl-acetate. Any mixture of a nonaqueous, i.e., organic, and aqueous solvent may be employed. Multi-assay plates that are resistant to such solvents include multi-assay plates made of glass, quartz, or other polymeric material resistant to nonaqueous solvents. Suitable quartz 8- or 96-well multi-assay plates are available from Hellena Laboratories, Beaumont Tex. and from Molecular Devices Corporation, Menlo, Park, Calif. (Part Nos. R1077 or R1076).

EXAMPLE 3

The method described in this example may be employed with any solvent, including solvents substantially free of water. For this method the absorbance spectrum of the desired solvent is determined in the NIR. Two wavelengths are then selected, a first wavelength near an absorbance maximum, denoted as $A_{max}$, of the solvent; and a second wavelength near an absorbance minimum denoted as $A_{min}$, of the solvent. The difference in absorbance of samples at the first and second wavelengths, $A_{max}-A_{min}$, should preferably be selected to be between 0.050 and 5.0. It is particularly preferred that the value of $A_{max}-A_{min}$ be selected to be between 0.1 and 1.0. The method is conducted as follows:

1A. Load the solvent employed to dissolve the analyte into a cuvette of known optical pathlength, for example, a 1 cm optical path cuvette. This optical pathlength is known as the Solvent Pathlength. Place the cuvette in a photometer and measure $A_{max}-A_{min}$. This parameter is referred to as Solvent $A_{max}-A_{min}$. (The cuvette may be stoppered and placed on its side in the light path of a vertical-beam photometer in order to make this measurement.

2A. Repeat step 1A, as described above in the same known optical pathlength cuvette with the analyte of interest now in the solvent. This parameter is referred to as Reference $A_{max}-A_{min}$. Also measure, approximately, the absorbance, $A_x$, of the analyte at the wavelength which will be used for subsequent measurements of analyte concentration. This parameter is referred to as Reference $A_x$. Preferably, absorbance of the analyte is between about 1.0 and 2.0.)

3A. Measure the values of $A_x$ in samples with the vertical-beam photometer. These parameters are referred to as Sample $A_x$. Also measure $A_{970}-A_{900}$ values of the sample samples with the vertical-beam photometer. The later parameter is referred to as Sample $A_{max}-A_{min}$.

The light absorption pathlength in each of the samples is determined from equation 7 as follows:

$$\text{Light Absorption Pathlength} = \frac{\text{Sample } A_{max} - A_{min} - \left\{ \frac{\text{Sample } A_x}{\text{Reference } A_x} [(\text{Reference } A_{max} - A_{min}) - (\text{Solvent } A_{max} - A)] \right\}}{\frac{\text{Solvent } A_{max} - A_{min}}{\text{Solvent Pathlength}}} \quad (7)$$

Light Absorbance per unit optical Pathlength for samples is determined using equation 8:

$$\text{Light Absorbance Unit Pathlength} = \frac{(\text{Sample } A_x) A_{max} - A_{min}}{\text{Solvent Pathlength}} \cdot \frac{1}{\text{Sample } A_{max} - A_{min} - \left\{ \frac{\text{Sample } A_x}{\text{Reference } A_x} [(\text{Reference } A_{max} - A_{min}) - (\text{Solvent } A_{max} - A)] \right\}} \quad (8)$$

In general, this method provides for determining the absorbance of an analyte per unite light absorption pathlength (or fraction of light transmitted by an analyte per unit light absorption pathlength) wherein the analyte is suspended or dissolved in a liquid solvent such that a relationship between light absorption of the analyte and the light absorption pathlength of the analyte are unknown. This method also provides for determination of the concentration of the analyte according to Equation (1) from (a) the absorbance of an analyte in the sample, (b) the light absorption pathlength of sample, and (c) a predetermined extinction coefficient of the analyte. If the analyte interferes with determination of the light absorption pathlength, or if solvents other than water are present the relationship between absorbance of the solvent or the amount of interference may be quantitated allowing a correct light absorption pathlength to be determined.

In general a first, a second and a third light signal resulting from, respectively, a first, second and third predetermined wavelength of light transmitted through substantially identical optical pathlength within a sample and wherein a difference between the first and the second light signals (e.g. $A_{970-910}$) is related to the light absorption pathlength and the third light signal (e.g. $A_{490}$, where Acid Orange 8 is the analyte) is related to both the light absorption pathlength and the concentration of the analyte. The light absorption properties of the sample solvent may be determined, independent of the analyte by measuring a forth and fifth light signal (e.g. $A_{970}$ and $A_{910}$) resulting from, respectively, the first and the second wavelength of light transmitted through a predetermined optical pathlength (e.g. 1 cm) of the solvent which is employed as a first reference liquid. Comparison of the difference in the first and second light signals (e.g. $A_{970}-A_{910}$ of the sample) and the forth and fifth light signals (e.g. $A_{970}-A_{910}$ of the solvent) allows the known light absorption pathlength of the solvent to be compared directly to the unknown light absorption pathlength of the sample.

Provided that the sample does not interfere with determination of the light absorption pathlength, the concentration of the analyte may be determined from absorbance of the sample at the third wavelength (e.g. $A_{490}$, where Acid Orange 8 is the analyte) or the fraction of light transmitted at the third wavelength per unit light absorption pathlength, from the predetermined light pathlength, the third light signal, the difference in the first and second light signal and the difference in the fourth and fifth light signals.

When the sample interferes with determination of the light absorption pathlength, the concentration of the analyte may be determined by measuring a relationship between absorbance of the analyte at the third wavelength and its (interfering) absorbance at the first and second predetermined wavelengths. Thus, a second reference liquid, containing the analyte, is prepared and used to measure a sixth and a seventh light signal resulting from, respectively, the first, second and third predetermined wavelengths of light transmitted through a predetermined light pathlength of the second reference liquid (e.g. $A_{970}-A_{910}$ of the second reference solution). The second reference liquid also is use to measure an eight light signal at the third predetermined wavelength (e.g. $A_{490}$, where Acid Orange 8 is the analyte). The effect of sample interference may be eliminated substantially from determination of light absorption pathlength according to the example shown in Equation 4. Similarly the effect of sample interference may be eliminated substantially from determination of light absorption per unit pathlength according to the example shown in Equation 5. Thus, the light absorption pathlength, light absorption per unit pathlength, fraction of light transmitted per unit pathlength, or concentration of analyte (according to Equation 1) may be determined from the predetermined light and from the first, second, third, fourth, fifth, sixth, seventh and eight light signals.

Preferably, the means for determining Light Absorption Pathlength and determining and indicating Light Absorbance per unit Optical Pathlength automatically are included in a vertical-beam photometric device capable of monitoring the optical density of samples contained in a multi-assay plate at a minimum of three (3) different center-band wavelengths of light. The device preferably will include means for determining and automatically indicating if the analyte presents significant interference with a simple, uncorrected, determination of Light Absorption Pathlength. An Interference Parameter, is determined using equation 9 as follows:

volume per well. Each sample and volume combination was tested in 8 replicate wells of the microplate.

The values of $A_{970}-A_{970}$ obtained experimentally were used to determine Light Absorption (i.e., optical) Pathlength for each well according to Eq. 2. FIG. 1 shows the volume of sample pipetted into each well vs. the mean Light Absorption Pathlength so determined and averaged for all wells of a given volume. The result shows that, for the 96-well NUNC microplate, the linear relationship described by equation 10 is observed:

$$\text{Light Absorption Pathlength} = [(2.82 cm/ml)(\text{Sample Volume})] - 0.0612 cm \qquad (10)$$

The correlation coefficient for this linear relationship was 0.9999. The inverse of this relationship is described by equation 11 for a 96-well NUNC microplate as follows:

$$\text{Sample Volume} = \frac{(\text{Light Absorption Pathlength} + 0.0612 \text{ cm}) \text{ ml}}{2.82 \text{ cm}} \qquad (11)$$

Equation 11 may be used to determine the approximate volume contained within the wells of such a multi-assay plate upon determining the Light Absorption Pathlength of the samples. Further, with suitable calibration, this procedure may be used to determine the volume contained in the wells of any type of assay plate. The wells of the microassay plates may be of various geometric shape, including flat-bottom, round-bottom (U-bottom), V-bottom, or any other shape. Any geometry or shape of wells in the multi-assay plate may be employed as long as the relationship between sample volume from the Light Absorption Pathlength is substantially reproducible. The relationship need not be linear, as is shown above for NUNC microplates which have cylindrical (flat-bottom) wells. It is only necessary to determine this relationship utilizing a multiplicity of known volumes of samples, and then determining Light Absorption $$\text{Interference Parameter} = \frac{\text{Sample } A_{max} - A_{min} - \left\{ \frac{\text{Sample } A_x}{\text{Reference } A_x} [(\text{Reference } A_{max} - A_{min}) - (\text{Solvent } A_{max} - A)] \right\}}{\text{Solvent } A_{max} - A_{min}} \qquad (9)$$

There are a variety of uses for the methods and devices of the invention. For example, the volume of samples collected from a fraction-collector in the wells of a multi-assay plate may be desired. In such a determination, the relationship between Sample Volume and Light Absorption Pathlength would be first determined according to any one of the methods provided above. This procedure is carried out in the following example.

EXAMPLE 4

The data established in Example 1 above were used to determine the relationship between Light Absorption Pathlength and Sample Volume in the Nunclon® Delta 96-well, flat-bottom multi-assay plates utilized in that Example. Measurements of $A_{970}-A_{900}$ were performed on six different chromophoric analytes, Acid Orange 8, Acid Orange 74, Azure B, Direct Yellow 62, Durkee Yellow Food Color, and Schilling Blue Food Color, in aqueous solvent. The sample solutions were dispensed into the wells of the multi-assay plate at either 350, 300, 250, 200, 150, or 100 µl sample Pathlength for the samples of known volume. This relationship may be used subsequently, together with Light Absorption Pathlength determinations in individual wells of multi-assay plates to estimate the liquid volume present within such plates.

EXAMPLE 5

This example demonstrates utility of the invention in the field of chromatography. Chromatography is used, generally, to separate analyte components in a sample mixture. Generally in chromatography, there exists a mobile phase and a stationary phase. The sample is applied in the mobile phase at the input of a means of retaining the stationary phase, e.g. a tubular column with a mesh support at the output of the column. As the mobile phase passes over the stationary phase the analytes bind to the stationary phase for more, or less time, depending on their affinity for the stationary phase, and therefore appear at different times at the output of the column. Separation of analytes in a sample is thereby accomplished when, "fractions" of the mobile phase, at the output of the column, are collected over time. In chromatography, generally, one wishes to analyze the amount, or concentration, of analyte present in each fraction collected. Furthermore, for reproducible chromatographic systems, carried out under constant conditions, e.g. constant temperature, constant stationary phase, constant mobile phase, constant flow rate, constant column volume, etc., the same analyte will usually appear at the same "elution volume," i.e. after the same volume of mobile phase has passed through the column. For such reproducible systems, one generally wishes to have a plot of the relative concentration of each analyte as a function of elution volume. The below example discloses utility of the instant invention in obtaining such "chromatograms" simply and conveniently while employing a vertical-beam photometer.

Certain, commercially-available fraction collectors may be employed conveniently to collect fractions directly in the wells of 96-well microplates such as the NUNC microplate employed above. For example, one such fraction collector is manufactured by the Gilson Corporation, Middleton, Wis. Generally, such fraction collectors collect fractions for a given time interval, or alternatively, such fraction collectors may count the droplets at the output of the chromatographic column and each fraction may contain a certain predetermined number of droplets. One problem is that each fraction contains a different, and unknown volume whenever the flow rate is not maintained constant for the timed interval method, and whenever the surface tension of the mobile phase is not maintained constant for the drop-counting method. Therefore, analysis of the fractions collected in a multi-assay plate by vertical-beam photometry will give absorbance values for each fraction that will be influenced both by the concentration of analyte present and by the volume of analyte present in the sample. The two variables, concentration and volume, thereby are confounded and a method for determining the two variables separately is needed. One method of the prior art is to manually measure the volume of each fraction, to withdraw a known volume from each well and transferring the withdrawn volume into a second multi-assay plate and to measure the optical density of each well in the second multi-assay plate. This prior art procedure suffers from the disadvantage that it is tedious, cumbersome, and prone to errors made during the volume-measuring and transferring steps. The method described below provides for a less tedious and cumbersome procedure and may be automated so as substantially to avoid errors.

In the present example, immunoglobulin (IgG) protein molecules were covalently-labeled with a fluorescent, fluorescein moiety. The reagent for labeling the protein was an NHS ester of fluorescein as provided in the Immuno-Ligand Assay Labeling Kit, Cat. No. R9002, Molecular Devices Corp., Menlo Park, Calif. The IgG was reacted with the labeling reagent at 40:1 molar ratio of reagent to protein in pH 7.0 phosphate-buffered saline (PBS) according to the instructions provided by the commercial supplier of the reagent. The reaction product, in 0.3 ml volume, was applied to a PD-10 column containing G-25 Sephadex® gel filtration media (Pharmacia, Uppsula Sweden) as the solid phase. The column was eluted with 0.1 ml aliquots of PBS applied successively to the top of the column. Each fraction was collected, into a separate well of a NUNC 96-well microplate, from the time of application of each 0.1 ml aliquot of PBS until the column ceased to flow. After the flow ceased, the microplate was output of the column was switched to a new well and the next aliquot of 0.1 ml of PBS was applied and the next fraction collected, etc.

Figure 2:
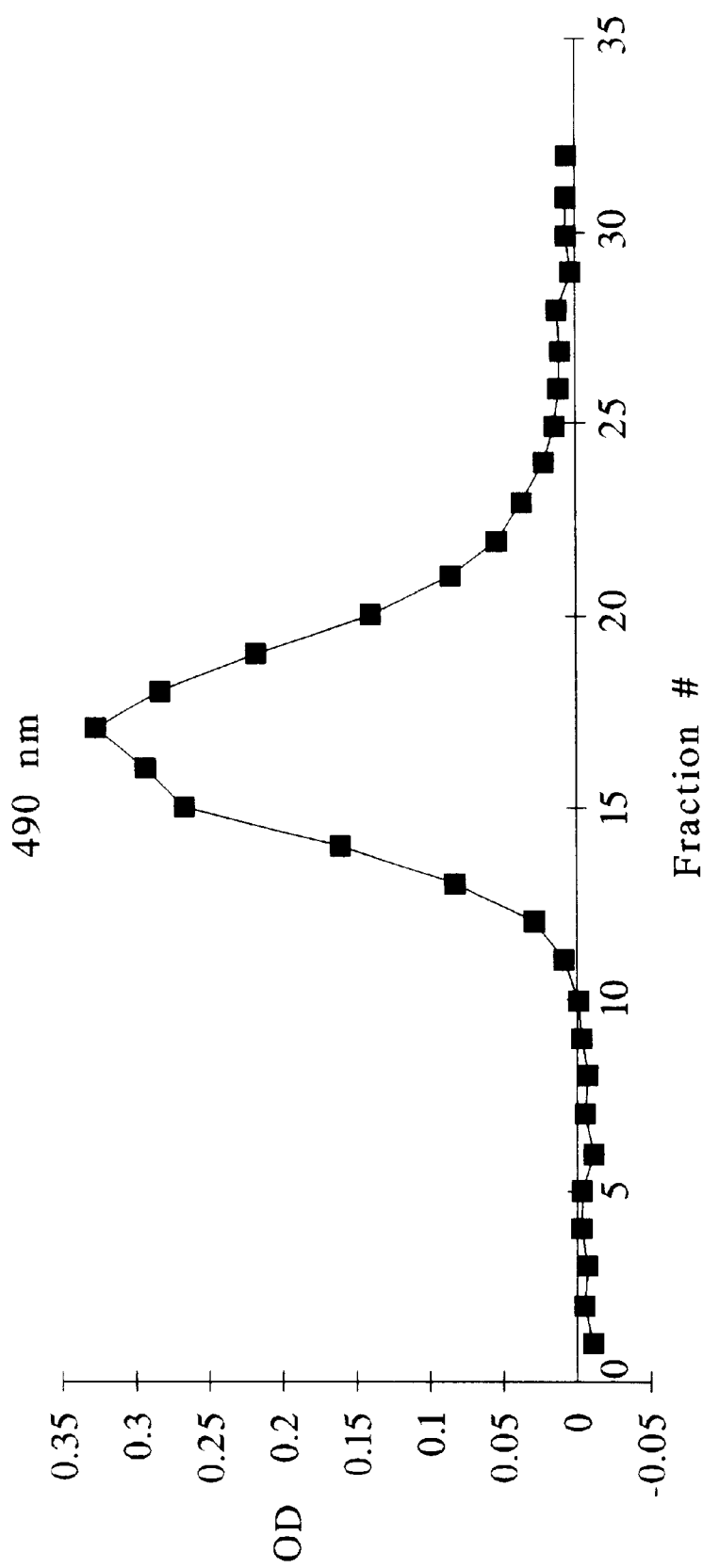
FIG. 2 is a graph showing the results of measuring the optical density of fractions at 490 nm in a vertical beam photometer.
Figure 3:
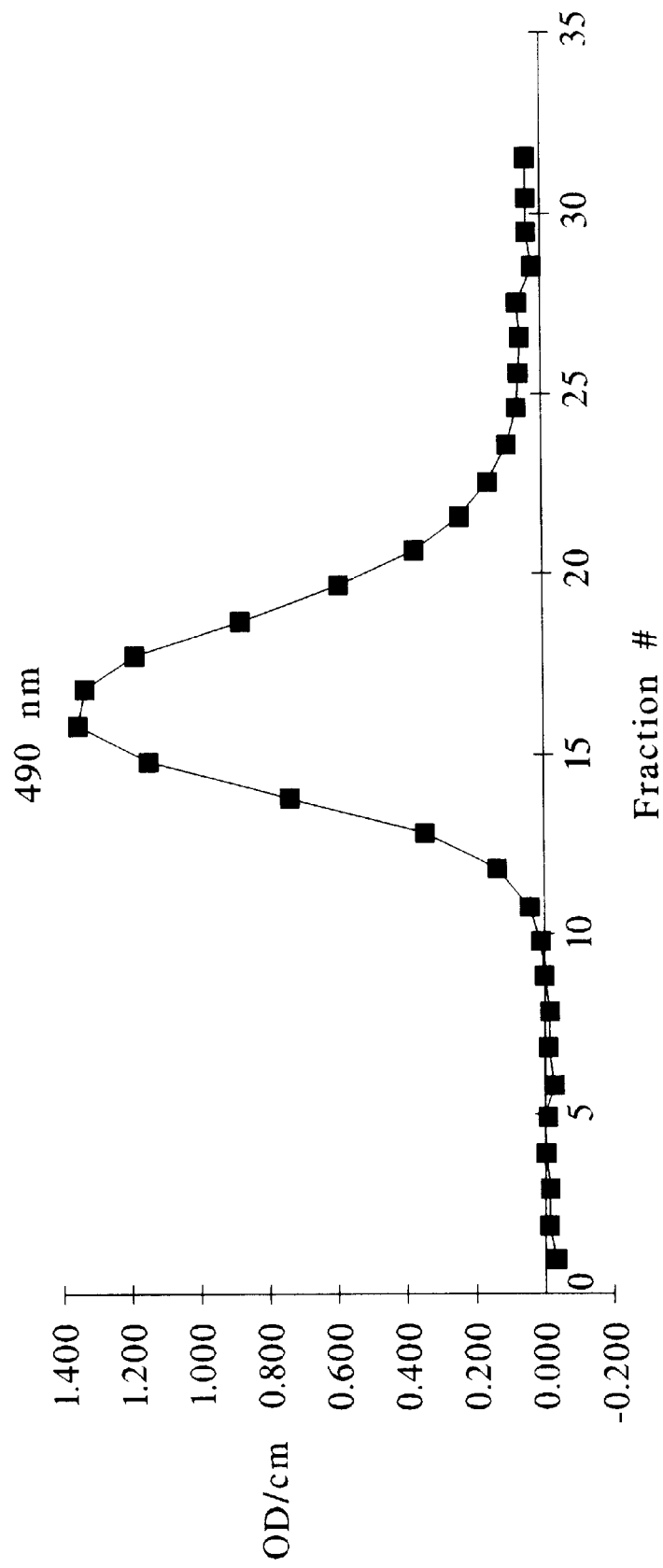
FIG. 3 is a graph of the results of measuring the optical density of fractions at 490 nm in a vertical beam photometer where the results have been corrected for the light absorption pathlength of each fraction so as to indicate optical density per unit (cm) optical pathlength of each fraction.

FIG. 2 shows the results of measuring the optical density of each fraction at 490 nanometers wavelength in a Spectramax 250 vertical-beam photometer (Molecular Devices Corporation, Menlo Park, Calif.). The first fraction was collected for analysis after discarding collecting the first 1.5 ml of PBS collected from the column. As seen in FIG. 2, a maximum in $OD_{490}$ was observed at fraction 17 where the labeled protein eluted from the column, as determined by similarly measuring the optical density of the fractions at 280 nanometers, also shows a maximum in absorption. Unreacted labeling reagent eluted from the column in subsequent fractions that are not shown in the figures. The shape of the curve shown in FIG. 2 was somewhat irregular. This irregularity, apparently, is not due to irregular variation in the concentration of IgG but is due to irregularity in the optical pathlength of the individual fractions. Shown in FIG. 3 are the same data corrected for light absorption pathlength of each fraction. The shape of the elution pattern of the labeled protein appears much more regular in FIG. 3, where the $OD_{490}$ per cm pathlength (i.e., the specific $OD_{490}$) is plotted for each fraction compared to FIG. 2 where only the $OD_{490}$ is shown. The light absorption pathlength in each fraction was determined by monitoring the difference in absorbance at 970 and 900 nanometer center-band pass wavelengths of near-infrared light in the Thermomax vertical-beam photometer and calculated according to equation 2.

Figure 4:
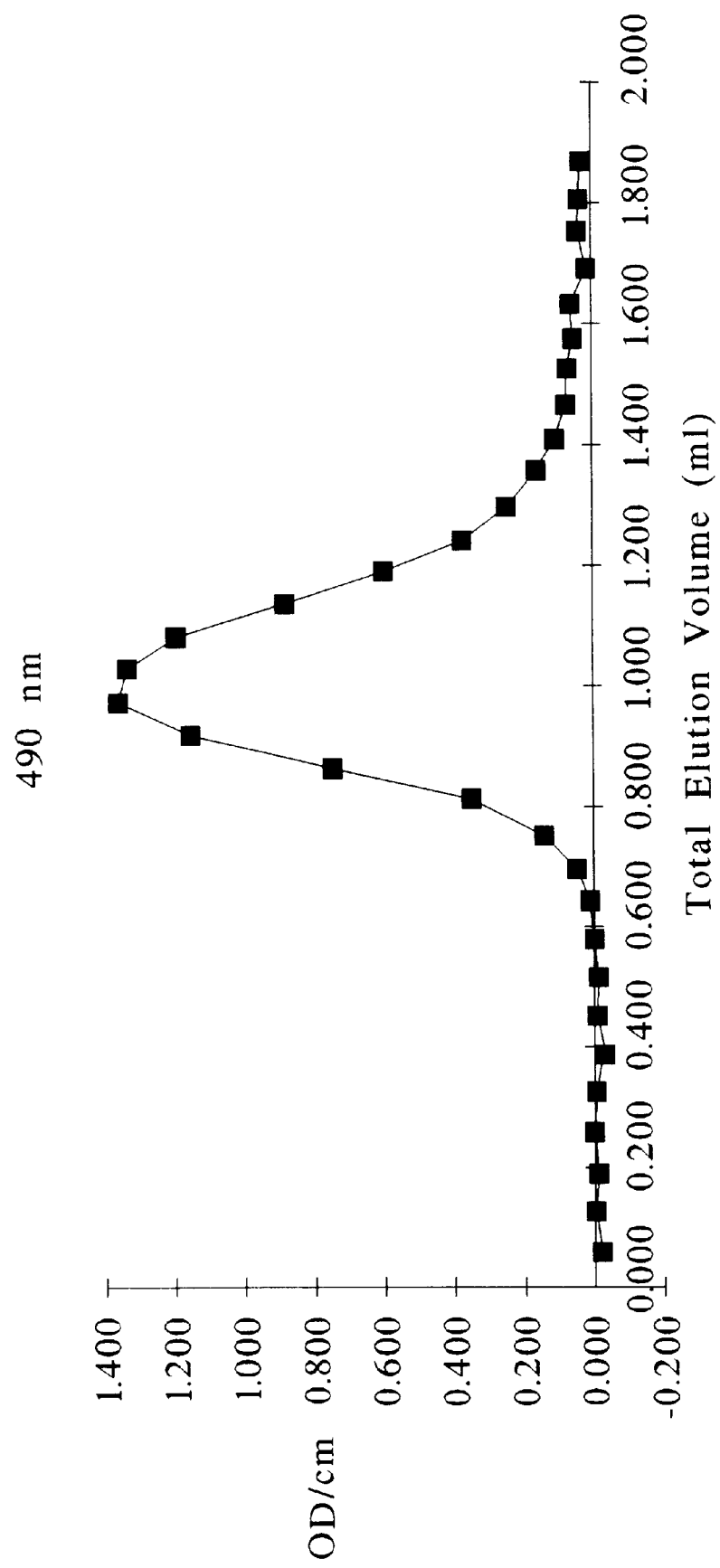
FIG. 4 is a plot of total elution volume versus the optical density measured at 490 nm for the combined volumes of the wells in a NUNC 96-well microplate.

Further shown in FIG. 4 is the same data shown in FIG. 3, except that the cumulative volume (after the first 1.5 ml eluted from the column) appears on the ordinate of the plot. The cumulative volumes were determined by employing the relationship of Equation 11, established for PBS in NUNC 96-well flat bottom microplates, to determine the volume of each fraction from the measured optical density difference at 970 and 900 nanometer center-band pass wavelengths and the light absorption pathlength values calculated from these data and equation 3. The volumes of each subsequent fraction then were summed to determine the cumulative elution volume. Each $OD_{490}$ per cm optical pathlength point is plotted at the mean cumulative elution volume of an individual fraction. The data appear similar to FIG. 3 in that the elution of the chromophoric protein molecules is seen to be smooth and regular.

EXAMPLE 6
Elimination of Error in Determination of Optical Pathlength due to Variation in Solvent Temperature Data has been gathered for a series of aqueous biological buffer solutions, which now permit further optimization of wavelength selection in the near infrared portion of the electromagnetic spectrum ("NIR") for use in determining optical pathlength of samples dissolved in such aqueous buffers. The NIR portion of the electromagnetic spectrum extends from 750 to 2500 nanometers wavelength. In this NIR range, light detection means may be detectors made of germanium, cadmium sulfide, lead sulfide, or the like. Preferably the measurement wavelengths will be between 750 and 1100 nanometers so that silicon photodetectors may be used as a light detection means. Silicon photodiodes generally are useful in the range of 180 nanometers to 1100 nanometers wavelength.

The following reagents were prepared: One-tenth molar (0.1 M) N-[2-Hydroxyethyl]piperazine-N'-[2-ethanesulfonic acid] (HEPES) was prepared from HEPES (1.0M) obtained from Sigma Chemical Co., St. Louis Mo. (Cat. No. H0887), by dilution into de-ionized water. One-tenth molar (0.1 M) Tris(hydroxymethyl) aminomethane (TRIS), pH 7.12, was prepared from 1.0 M TRIS obtained from BioRad Laboratories, Hercules, Calif. (Cat. No. 161-0719), dilution into de-ionized water. The 0.1 M sodium phosphate was prepared by mixing 61 ml of 1.0 M sodium phosphate monobasic, (Cat. No. S369-1) and 39 ml of sodium phosphate dibasic, (Cat. No. S374-500) each from Fisher Scientific Pittsburgh, Pa. and diluting into de-ionized water. Threshold Assay Buffer was prepared by dilution of Concentrated (10×) Threshold Assay Buffer obtained from Molecular Devices Corporation, Sunnyvale, Calif., (Cat. No. R3030-1) and diluted to 1× (pH 7.02) in de-ionized water. Dulbecco's phosphate buffered saline solution, pH 7.23 (PBS), was obtained from Irvine Scientific (Cat. No. 9236). One-tenth molar (0.1 M) 2[N-Morpholino] ethanesulfonic acid (MES) buffer, pH 6.14, was prepared from MES obtained from Sigma Chemical Company (Cat. No. M-8250) in deionized water.

Figure 5:
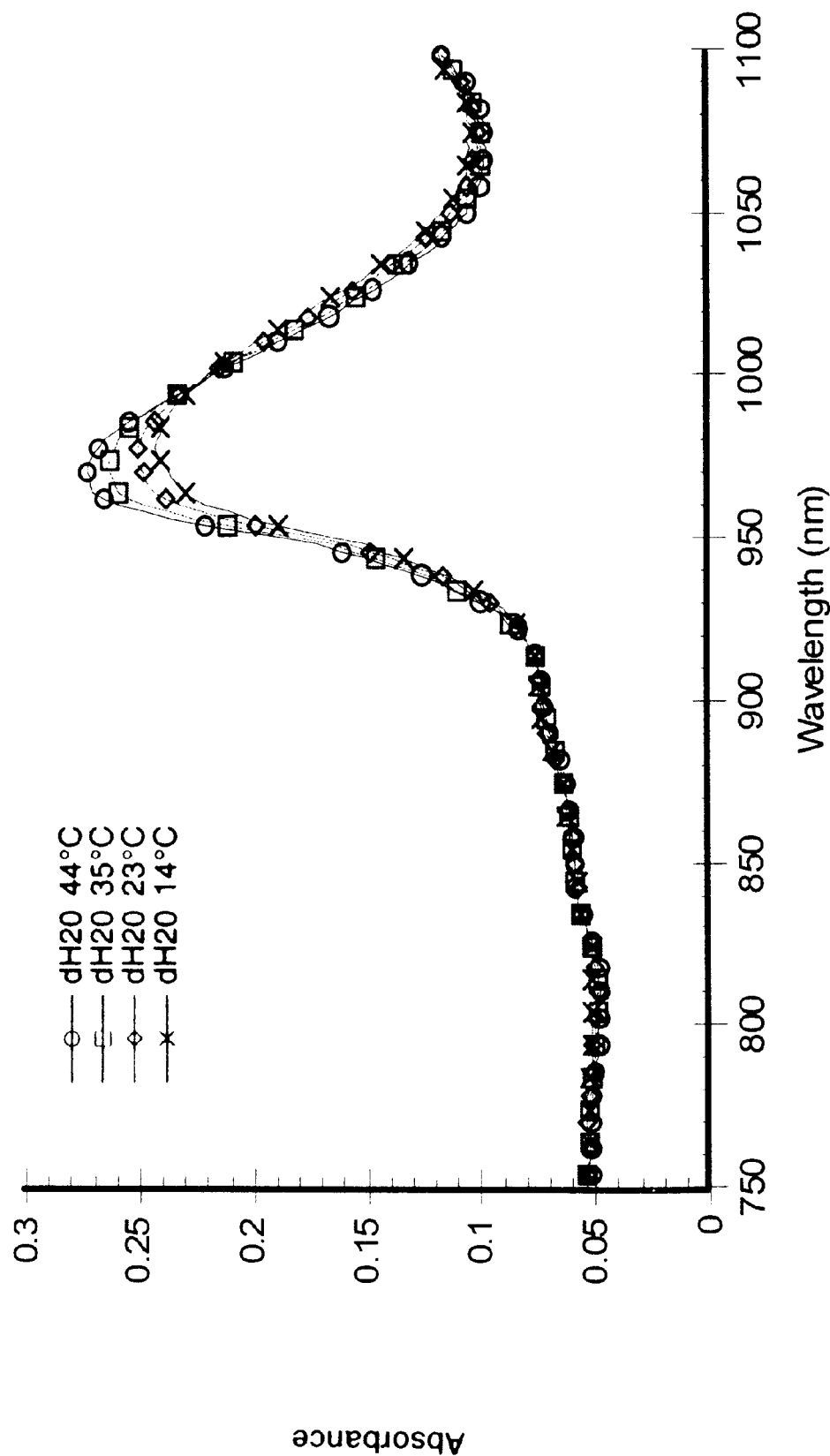
FIG. 5 is a graph showing the absorption spectrum of pure water between 750 nm and 1100 nm at four different temperatures.

FIG. 5 shows the absorption spectrum of pure water between 750 and 1100 nanometers at 4 different temperatures, i.e. 14° C., 23° C., 35° C. and 44° C. The spectra were taken in an ATI Unicam UV-2-100 Double Beam Scanning UV-Visible Spectrometer with a 2.0 nanometer fixed bandwidth. The data were taken under the control of a Compaq 386 computer running ATI Vision software set to take spectral data in the "Survey" mode at "Intelliscan" speed. Approximately 3 ml samples were placed in Spectro Clear™ acrylic precision spectrophotometer cuvettes, with a light absorption pathlength of 1.00 cm, obtained from Centaur Science, Inc., Stamford, Conn., (Cat. No. SCA-20) in the sample beam of the spectrophotometer. The reference beam contained no sample or cuvette. (Measurements made in this configuration are said to employ an "air blank").

FIG. 5 also shows that between 900 and 917 nanometers there is relatively little absorbance of the water sample. Between 960 and 980 nanometers there is a peak of maximal absorbance of the water sample. The wavelength of maximal absorbance ($\lambda_{max}$), as well as the absorbance at $\lambda_{max}$, changes as a function of temperature. For example, at 974 nanometers which is near $\lambda_{max}$, the absorbance changes by about 0.4% per degree centigrade. Thus, in order to obtain ±1% precision in determination of optical pathlength, the temperature must vary by no more than ±2.50° C.

In contrast, at about 998 nanometers pure water gave a nearly constant optical density of about 0.14 at all four temperature values. Thus, the wavelength region near 998 nanometers (e.g. the wavelength region from 998 to 1008 nanometers) is a region where optical properties of pure water are nearly independent of temperature. For the present, we shall call such a wavelength region an "isosbestic wavelength region," which for pure liquid water occurs near 998 nanometers as a function of temperature.

Figure 6:
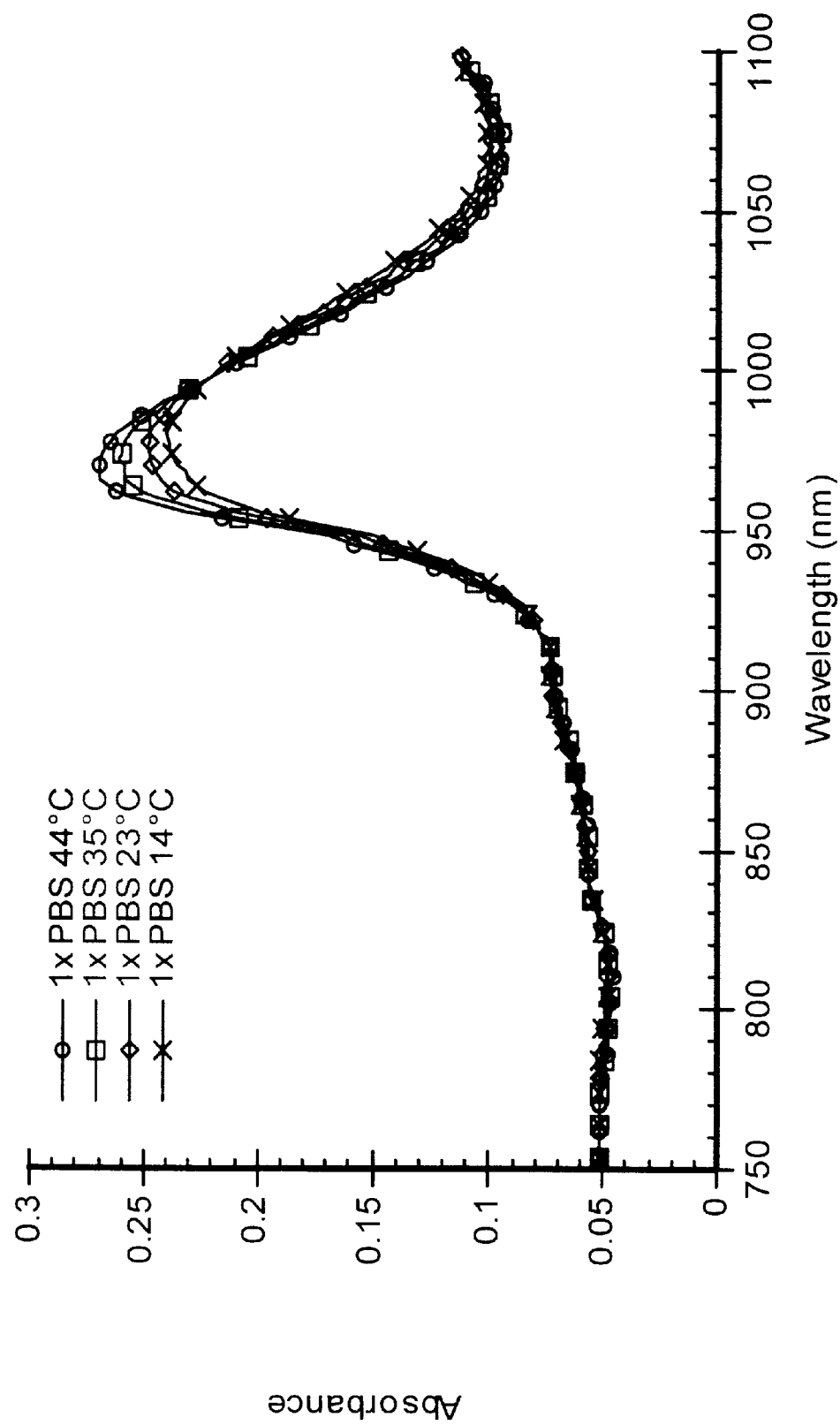
FIG. 6 is a graph of the near infrared (NIR) portions of the electromagnetic spectrum for a biological buffer solution, Dulbecco's phosphate-buffered saline (PBS).

FIG. 6 similarly shows the NIR absorption spectrum of Dulbecco's phosphate-buffered saline (PBS) containing 200 mg/l potassium chloride, 200 mg/l potassium phosphate monobasic, 8000 mg/l sodium chloride and 1158 mg/l sodium phosphate dibasic, pH 7.23 which is commonly-used biological buffer solution. The absorption spectrum is strikingly similar to that of pure water seen in FIG. 5. The NIR absorption spectrum for isotonic (0.155 M) sodium chloride; 0.1 M phosphate, pH 7.0 and 0.1 M RIS, 0.1 M HEPES, 0.1 M MES and Threshold Assay Buffer similarly were recorded at 14° C., 23° C., 35° C. and 44° C. In each case the NIR absorption spectra (not shown) are virtually indistinguishable from that of pure water (i.e. less than 3% different in relative absorption intensity at any wavelength). The isosbestic behavior, as a function of temperature in each case is observed near 998 nanometers.

Table III shows optical density values, determined at several selected wavelengths, each at the 4 selected temperature values, for each aqueous buffer solution. Also shown in Table III are the results of taking the difference in optical density measured at 998 nanometers and optical density measured at either 900 or 910 nanometers, i.e., ($OD_{998}$–$OD_{900}$) or ($OD_{998}$–$OD_{910}$) for each aqueous buffer solution at each temperature. The results show that for the 8 different samples, the ($OD_{988}$–$OD_{900}$) and ($OD_{998}$–$OD_{910}$) were remarkably constant at all temperature values. The ($OD_{998}$–$OD_{900}$) values ranged from 0.138 to 0.133, i.e. a range of 3.6%. The ($OD_{998}$–$OD_{910}$) values ranged from 0.136 to 0.132, i.e. a 2.9%. Thus, interferences or inaccuracies in determining optical pathlength though liquid samples can be eliminated substantially by:

1.) measuring a first optical density value of the samples in a first "isosbestic wavelength region",
2.) measuring a second optical density value of the samples in a second "isosbestic wavelength region", and
3.) determining the difference in the first and second optical density values.

Preferably, the absorption coefficient of the sample is substantially different in the first and second wavelength regions. For example, as shown in FIGS. 5 and 6 and Table III, for aqueous samples a "isosbestic wavelength region" occurs about 998 nanometers (generally from 993 to 1002 nanometers, and more generally from 988 to 1008 nanometers). A second isosbestic wavelength region occurs about 910 nanometers (generally from 900 to 910 nanometers, and more generally from 750 to 930 nanometers). Alternatively, a second isosbestic wavelength region occurs near 1090 nanometers (generally from 1080 to 1100 nanometers and more generally from 1050 to 1150 nanometers).

When employing ($OD_{998}$–$OD_{910}$) values to measure optical pathlength, a value of 0.135 cm$^{-1}$ (generally from 0.140 to 0.130 cm$^{-1}$) may be used to calculate optical pathlength through substantially aqueous samples. For example, if a ($OD_{998}$–$OD_{910}$) value of 0.135 is determined for aqueous samples with an unknown optical pathlength, the unknown optical pathlength is calculated to be 0.135/0.135 cm$^{-1}$, i.e. 1 cm. Similarly, if an ($OD_{998}$–$OD_{910}$) value of 0.100 is determined, then the unknown optical pathlength is 0.100/0.135 cm$^{-1}$, i.e. 0.741 cm. As another example, optical pathlengths through substantially aqueous samples may be determined from any measured ($OD_{998}$–$OD_{900}$) value by employing the constant 0.137 cm$^{-1}$ (instead of 0.135 cm$^{-1}$) in a similar fashion. As a third example, optical pathlengths through substantially aqueous samples may be determined from any measured ($OD_{998}$–$OD_{1090}$) value by employing the constant 0.110 cm$^{-1}$ in a similar fashion.

EXAMPLE 7

Elimination of Error in Determination of Optical Pathlength due to Variation in Solvent Composition In this example, NIR absorption spectra, between 750 and 1100 nanometers, were acquired as described in Example 6. The samples were maintained near room temperature (at about 23° C.).

Figure 7:
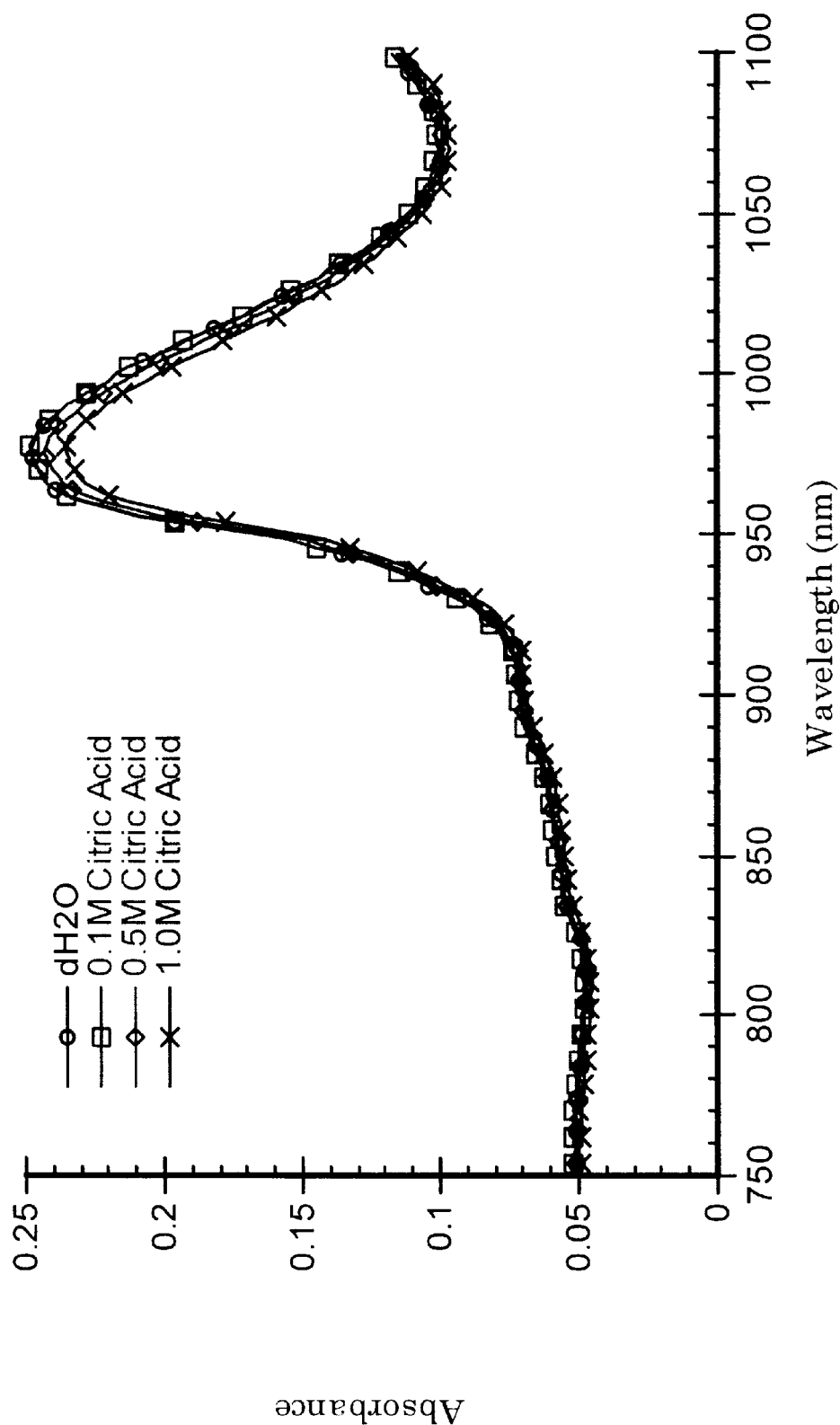
FIG. 7 is a graph of the results of the near infrared (NIR) portion of the electromagnetic spectrum for pure water and 0.1 m, 0.5 m and 1.0 m citrid acid solutions in pure water.

FIG. 7 shows the NIR absorption spectra of pure water, 0.1 M, 0.5M, and 1.0 M citric acid solutions (in pure water). The citric acid solutions show significant deviation from the spectrum of pure water. The deviation increases with increasing concentration and is greatest at the 1.0 M, citrate concentration.

Figure 8:
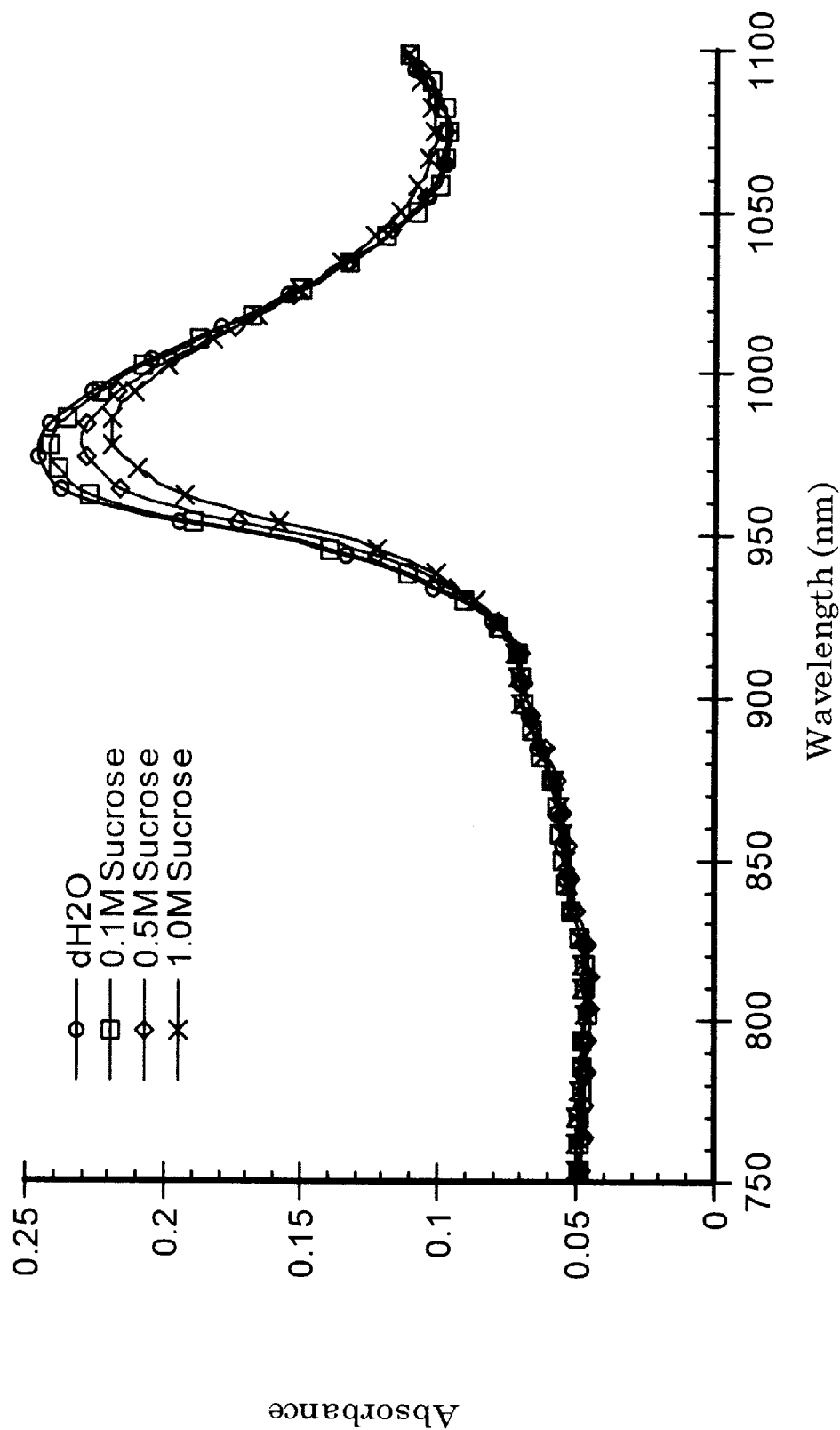
FIG. 8 is a graph of the results of the near infrared (NIR) portion of the electromagnetic spectrum, between 750 nm and 1100 nm, of either pure water, 0.1 m, 0.5 m or 1.0 m sucrose solutions in pure water.

FIG. 8 similarly shows the NIR absorption spectra, between 750 and 1100 nanometers, of either pure water, 0.1 M, 0.5 M, or 1.0 M sucrose solutions (in pure water). Similar to the citric acid solutions, the sucrose solutions show significant deviation from the spectrum of pure water. As for citrate, the deviation increases with increasing solute concentration and is greatest, 1.0 M, concentration. The deviation caused by sucrose is even more pronounced than that caused by citrate. The value of ($OD_{970}$–$OD_{910}$) is about 20% less for 1.0 M sucrose compared to pure water. Significantly better, the value of either ($OD_{998}$–$OD_{910}$) or ($OD_{998}$–$OD_{900}$) are only about 9% less for 1.0 M sucrose compared to pure water. While significant improvement in determining optical pathlength is obtained by measuring absorption of light in the "isosbestic wavelength region" near 998 nanometers, substantially complete elimination of error in such determinations, with all aqueous samples, however, is not possible.

EXAMPLE 8

Incorporation of a Reference Solvent Liquid of Known Optical Pathlength

In order to substantially eliminate errors in determination of unknown optical pathlength of sample solutes dissolved at high concentration in a solvent liquid, an improved method with the following steps is employed:

1. Place a reference comprising a reference sample solvent in a known optical pathlength, and a sample, comprising a sample in the sample solvent, in an unknown optical pathlength, and
2. Measure:
   a.) a first optical density value ($A_{REF\lambda 1}$) of the reference sample solvent at a first preselected wavelength in the NIR where the sample analyte does not absorb light substantially and where absorption of light by the sample solvent is near a local maximum (for example in the region of 960 to 1000 nanometers for an aqueous solvent), and
   b.) a second optical density value ($A_{REF\lambda 2}$) of the reference sample solvent samples at a second preselected wavelength in the NIR where neither the sample analyte nor the reference sample solvent absorb light substantially (for example in the region of 900 to 910 nanometers, or the region from 1060 to 1080 nanometers, for an aqueous solvent), and
   c.) a third optical density value ($A_{REF\lambda 1}$) of the sample at the first preselected wavelength, and
   d.) a fourth optical density value ($A_{REF\lambda 2}$) of the sample at the second preselected wavelength, and
3. Calculate the optical pathlength as:

Sample Light Absorption Pathlength=Reference Light Absorption Pathlength

EXAMPLE 9

A Device Incorporating a Reference Solvent Liquid of Known Optical Pathlength Advantageously, a device will enclose both the reference and the sample so that the temperature of the reference and the sample will be substantially the same temperature, generally within a range of 2° C. and more generally with a range of 5° C. Also advantageously, the device will enclose a multiplicity of samples, e.g. an 8×12 array of samples in a 96-well multiassay plate, at a multiplicity of sample sites maintained at substantially the same temperature as the reference. A prepared embodiment of the present invention is herein described. The device was used in following method steps 1–3 and Equation 4 and 5 in Example 2. The device measures unknown optical pathlengths of multiplicity of assay sites with the aid of an incorporated reference liquid of known optical pathlength. In operation, a user performs the following operations:

(a.) The reference liquid is placed in a cuvette, of known optical pathlength, within the device. The reference liquid is preselected to be similar in composition and temperature to the samples. (Optimally, the samples will be present in the reference liquid).

(b.) Next, the samples on a multiassay plate, are placed in the device so that the samples and the reference liquid are maintained at substantially the same temperature (to within 1–2° C.). [Note that the original Case 94,373 patent application does not mention that the temperature of the reference liquid and unknown liquid samples should be controlled.]

(c.) The device measures the transmission of NIR light through each of the liquid samples and through the reference liquid of known optical pathlength.

(d.) The device compares the transmission of light through both the samples and the reference liquid and calculates the optical pathlength of the samples.

Having determined the optical pathlength through each of the samples in a multi-assay plate, the device also may be used to determine the concentration of analytes in such samples by determining the absorbance of the analytes at a preselected wavelength. The results of such determinations, therefore, may new be expressed in terms of optical density per unit pathlength, e.g. $A \cdot cm^{-1}$. Customarily, the results will be expressed in optical density per 1 cm pathlength. For example, if the sample material absorbs at 405 nanometers wavelength and the optical density of the sample at 405 nanometers, $A_{405}$, if determined by the device to be 0.150 O.D. units; and the optical pathlength of the sample, determined by steps a–d above is determined to be 0.5 cm, then the calculated $A_{405} \cdot cm^{-1}$ value will be 0.300.

Once the optical pathlength is known, the concentration of analyte may be determined by the Beer-Lambert Law given in equation (1), from the extinction coefficient $\epsilon\lambda$ at a preselected wavelength $\lambda$ and from the absorbance of the analyte at the preselected wavelength $\lambda$.

Figure 9:
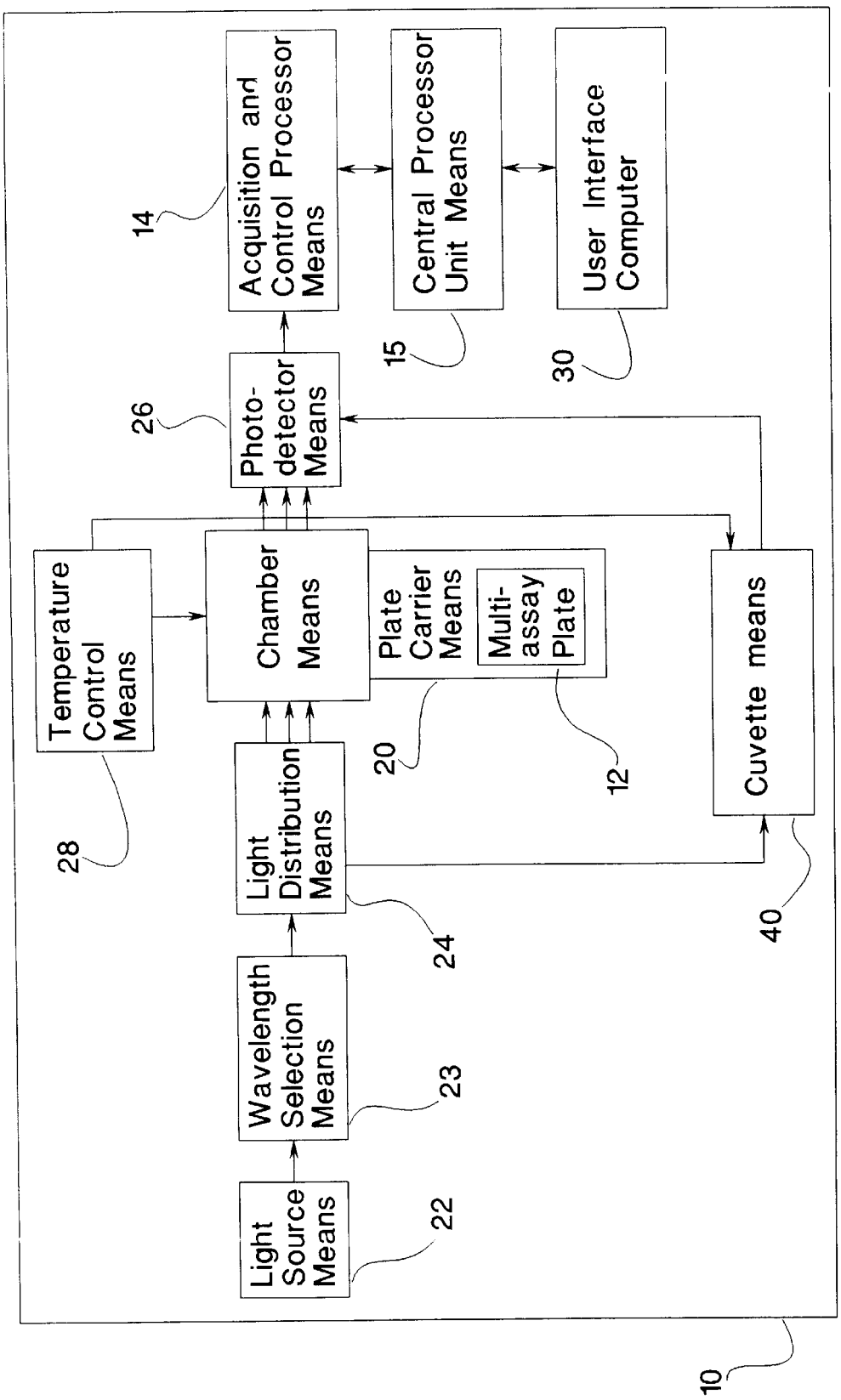
FIG. 9 is a schematic representation of the device of the present invention.

A photometric measuring system 10 having a multiplicity of sample sites with unknown optical pathlength and at least one reference site of known optical pathlength is shown in FIG. 9. The system 10 is comprised of a light source means 22 which directs light to a wavelength selection means 23, which causes substantially monochromatic light to pass into a light distribution means 24. The light distribution means 24 directs light to:

a) a reference optical pathlength of known pathlength, shown in FIG. 9 as a cuvette means 40. Light transmitted by the reference is detected by a photodetector means 26, and b) a chamber means 16 which encloses the multiplicity of samples contained at a multiplicity of sample sites on a multi-assay plate 12.

The multi-assay plate 12 is carried by a plate carrier means 20 so as to position the sample sites so that light directed by the light distribution means 24, and transmitted by the samples is detected by the photodetector means 26. A temperature control means 26 controls the temperature within the chamber means 16 and the cuvette means 40.

Electrical signals from the photodetector means 26 are sent to an acquisition and control processor means 14 which is in electrical communication with a central processor unit means 15. The central processor means 15 may send data directly to a printer and be controlled by a user. Advantageously, however, the central processor means 15 will be interfaced to a user interface computer 30, which enables the user to control the system 10, acquire data, visualize data, compute data parameters from the acquired data, and ultimately to export the data or parameters to an external printing device.

Figure 10:
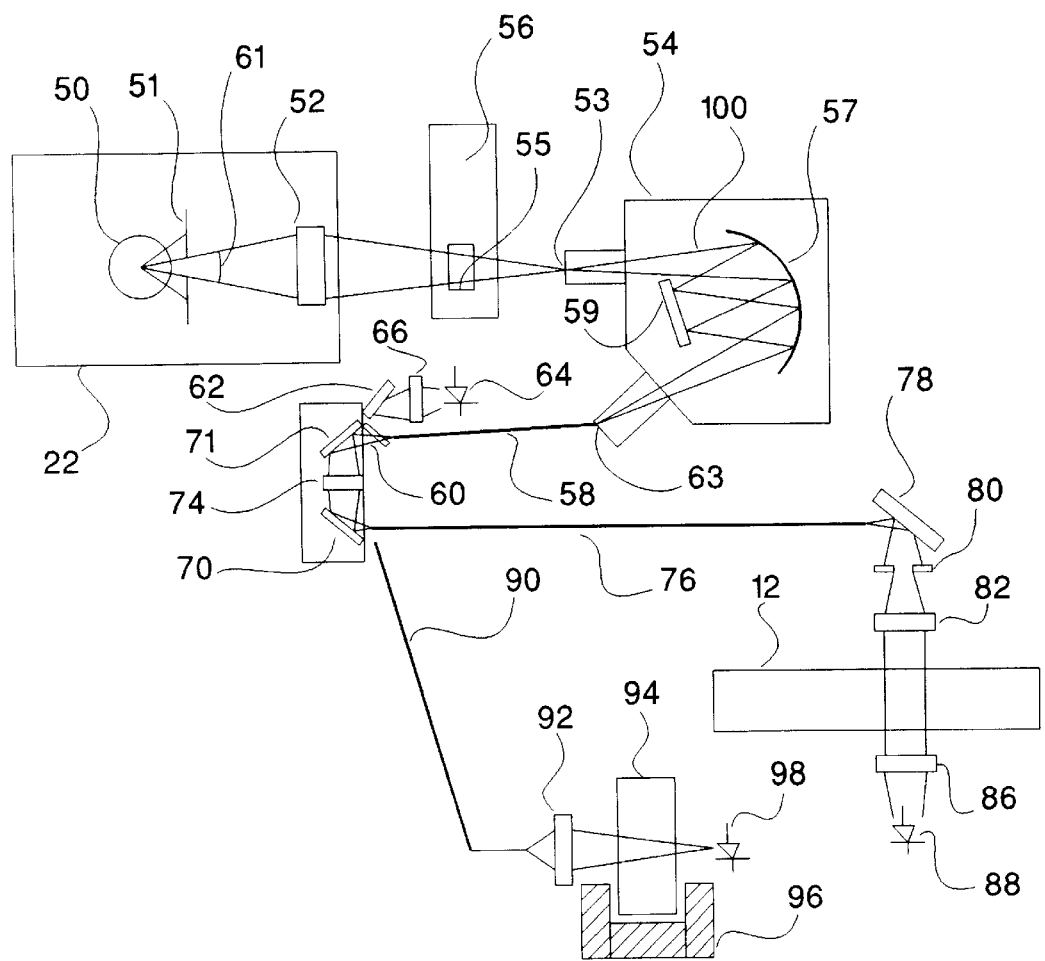
FIG. 10 is a schematic representation of a preferred embodiment of the present invention.

FIG. 10 is a detailed description of a preferred embodiment of the photometric measuring system 10. Except for the disclosure given below, the preferred embodiment is identical to the preferred device disclosed in U.S. patent application Ser. No. 08/228,436 filed Apr. 15, 199, which is incorporated herein by reference. The system 10 produces a beam of substantially monochromatic light, in the form of flashes, and delivers this light sequentially to a plurality of light channels, eight in the preferred embodiment, to sequentially illuminate the fluid samples in the multiassay plate 12.

An excitation light source 50, such as a xenon flash lamp, emits light flashes containing wavelengths between at least 200 nanometers and 1100 nanometers. Light from the excitation light source 50 beams through an aperture 51 limiting the light arc (61) to approximately ten degrees (10°). This light then passes through a source lens 52, which focuses the light through one of a series of filters 55, included on a filter wheel 56, upon a monochrometer, generally designated 54. The excitation light source 50, aperture 51, and source lens 52 cooperate to define the light source means 22.

The source lens 52, in this preferred embodiment, is a fused silica plano-convex lens with a 12.7 millimeter diameter, a 16 millimeter focal length, and an optical magnification of 1×. The source lens 52 is spaced 32 millimeters from the excitation light source 50 and 32 millimeters from the entrance slit 53 where light enters the monochrometer 54. A collimating/focusing mirror 57 reflects and collimates the light beam onto a rotatable diffraction grating 59. There the light is dispersed at an angle with respect to the grating. This angle is dependent upon the wavelength of light striking the grating. The dispersed light falls back on the collimating/focusing mirror 57 which focuses substantially monochromatic light, within a narrow wavelength band, upon an exit slit 63. Thus, the wavelength of substantially monochromatic light passing through exit slit 63 is dependent upon the wavelength of light and the angle of the grating 59 with respect to the collimated light beam. The wavelength of maximal intensity of light passing through the exit slit may be preselected by rotating the grating 59 with respect to the incident light coming from mirror 57. The bandpass of monochromatic light passing through exit slit 63 is dependent principally upon the optical distance from grating 59 to exit slit 63, as well as the widths of exit slit 63, entrance slit 53 and aperture 51.

Exit slit 63 preferably, 0.7 in width and 1.3 millimeters in height, is formed by a metal end cap forming the end of a bundle of optical fibers 58 which accepts the substantially monochromatic light. Cooperating to define the wavelength selection means 23 are filter wheel 56, optical filters 55, and monochrometer 54. The output of monochromator 54 provides light having a predetermined, continuously selectable, second wavelength range within the first wavelength range provided by light source 50. In the preferred embodiment disclosed herein, the second wavelength range has a predetermined bandpass width, defined as the wavelength width at one-half maximum light transmission, of about 4 or 5 r nanometers for all center-band wavelengths continuously selectable by the user between 250 and 750 nanometers. The bandpass width may be predetermined within a wider range of about 1 to 20 nanometers by changing the width of the exit slit 63, e.g. by employing a mechanically adjustable slit as the exit slit 63.

In the preferred embodiment optical fiber bundle 58 includes nineteen (19) optical fibers each 200 millimeter in diameter with a numerical aperture of 0.22, each arranged at the input in three (3) rows of six (6), seven (7), and six (6) fibers. This effectively defines a 0.7 millimeter by 1.3 millimeter rectangular exit slit 63. The output of the optical fiber 58 is configured as a circle with a diameter of 1.3 millimeters. Light from the output of fiber 58, which is emitted over a solid angle of about ten degrees, is split by a beam splitter 60, a sapphire window in this preferred embodiment. The beam splitter 60 splits the light into a test light that passes through the beam splitter 60 to a rotor assembly 70 and a reference light that reflects from the beam splitter 60 to a flat reference mirror 62. The reference mirror 62 reflects the reference light through a reference lens 66 to a reference photodetector 64 of the photodetector means 26. The reference lens 66 is a bi-convex lens, is made of fused silica, has a focal length of 6.8 millimeters, and has a diameter of 6.8 millimeters.

The intensity of light flashes emitted by the Xenon flash light 50 may vary by as much a 50% between successive flashes due to variations in the energy and position of the flash arc within the flash lamp. The reference photodetector 64 outputs an electrical signal; representative of the amplitude of the monochromatic light carried by the optical fiber 58 for each flash of the light excitation source 50. This electrical signal is used as an intensity reference for the reading of sample light transmitted through samples in the multi-assay plate 12.

The rotor assembly 70 includes two substantially identical rotor mirrors 71 and 72 to redirect the light by 180° (degrees) and a rotor lens 74 to focus the light beam between the rotor mirrors 72. The rotor mirrors 71 and 72 and rotor lens 74 act to reduce the spot size of the light beam from 1.3 millimeter diameter at the input of the rotor assembly 70, which is the output of the optical fiber 58, to 0.65 millimeters at the output, which is the input of a selected one of nine (9) receiving optical fibers 76 or the input of a reference distribution optical fiber 90. The reduction in light beam diameter within the rotor 70 allows substantially all of the light to be launched at a solid angle of about 20° into the receiving fibers 76 of the light distribution means 24, greatly enhancing efficiency of sample light transmitted through the rotor 70. Care is taken so that the sample light is not focused in such a way that it exceeds the numerical aperture of the receiving optical fibers 76 and 90 which will accept light over a solid angle of about 24°.

The optical distribution channels are defined by the receiving optical fibers 76 and 90, made of solid silica or quartz, 1 millimeter in diameter, with a numerical aperture of 0.22. Light from the sample distribution optical fibers 76 reflects off a sample light mirror 78, made of $MgF_2$ with a flat surface, into a substantially vertical sample light distribution direction. A sample light aperture 80 further limits the numerical aperture of the light beam. A sample light lens 82 and a sample light photodetector lens 86, each a bi-convex lens made of fused silica with a 6.8 millimeter focal length and a 6.8 millimeter diameter, further focus the sample light. For ease of illustration, FIG. 10 shows only one of a series of eight substantially identical sample light distribution optical fibers 76, sample light mirrors 78, sample light apertures 80, sample light lenses 82 and sample light photodetector lenses 86.

A reference pathlength distribution optical fiber 90 directs light distribution optical fiber directs reference pathlength light from optical rotor 70 to reference pathlength lens 92, through a reference cuvette of known optical pathlength 94, which is retained in place by a cuvette holder 96. Cuvette 94 and cuvette holder 96 cooperate to define cuvette means 40. Reference pathlength light transmitted through cuvette 94 is detected by reference pathlength photodetector 98.

In operation, first a reference sample solvent is placed in the reference cuvette of known optical pathlength (e.g. a 1.00 cm optical pathlength) and samples in the sample solvent are place in one, or more, wells of the multi-assay plate 12. The multi-assay plate is then place on a plate carrier means 20 within chamber means 16. The user instructs the system 10 to "read" one-or-more preselected samples. The plate carrier means positions the preselected samples between the sample light lenses 82 and sample light photodetector lenses 86 so that light from the sample distribution optical fibers 76 will pass substantially vertically through the samples without striking the side-walls of the multi-assay plate, which contains the samples.

In a reading cycle the rotor assembly 70 first rotates so as to distribute light to a dark channel, so that no light falls upon sample photodetectors 88 or pathlength reference photodetector 98 when light source 50 emits a flash of light. Electrical signals from sample photodetectors 88 and pathlength reference photodetector 98 when the light is distributed to a dark channel, thus provides a zero light baseline value for each photodetector. The rotor assembly 70 secondly rotates so as to distribute reference pathlength light through the reference cuvette 94, which contains reference sample solvent in a known optical pathlength. The reference cuvette is retained in place by a cuvette holder 96. Reference pathlength light transmitted through cuvette 94 is detected by reference pathlength photodetector 98 which, in turn, sends an electrical signal related to the intensity of detected light to acquisition and control processor means 14.

The rotor assembly 70 next rotates to sequentially illuminate the series of eight sample light distribution optical fibers 76 so as to sequentially illuminate the fluid samples in the multiassay plate 12. The multiplicity of samples receives sample light having a substantially identical spectral distribution of light intensity provided by monochrometer 54. The photometric device 10 described provides the above sample light characteristics to a multiplicity of samples in a multi-assay plate within a short period of times so that the optical properties of 96 samples contained in a conventional 8×12 microplate may be determined within approximately 9 seconds (generally from 8 to 10 seconds). Determination of optical pathlength requires measurement at least 2 different wavelengths, $\tau 1$ and $\tau 2$. Thus, in order to measure optical pathlength through the samples the measurement procedure is first performed at $\tau 1$ and then repeated at $\tau 2$, thus the measurements is completed within 18 seconds (generally from 16 to 20 seconds).

EXAMPLE 10

Elimination of Error in Determination of Absorbance of Samples per Unit Optical Pathlength The device disclosed in Example 9 may be use to substantially eliminate error in the determination of the ratio of absorbance of analytes within liquid samples and the optical pathlength. These ratiometric measurements are given as "Light Absorbance per Unit Pathlength" in Examples 2 and 3 above.

In order to perform such ratiometric measurements, the device additionally monitors the absorbance of an analyte, in the one or more samples sequentially, at a preselected wavelength. This value is given as "Sample $A_x$" in examples 2 and 3 above. The device then computes the ratio of $A_x$ and the optical pathlength, for each sample, to give "Light Absorbance per Unit Pathlength".

The disclosed invention comprises photometric methods and devices for determining Light Absorption Pathlength of liquid samples containing analytes dissolved or suspended in a solvent. The methods and devices rely on determining a relationship between the light absorption properties of the solvent and the optical pathlength of liquid samples containing the solvent. This relationship is used to establish the Light Absorption Pathlength for samples having an unknown Light Absorption Pathlength, but having a similar solvent composition. Such samples, for example, may be contained within a plurality of wells disposed in a multiassay plate, such as a 96-well microplate, in a vertical-beam photometer. Such vertical-beam photometers are able to measure absorbance of analytes, within such samples, at predetermined wavelengths of light. According to the invention such vertical-beam photometers may automatically determine and indicate, to an analyst carrying out a chemical measurement, the concentration of an analyte. The automatic determination is made, according to Equation (1), from (a) the absorbance of the analyte in the sample, (b) the Light Absorption Pathlength determined according to the invention, and (c) a predetermined extinction coefficient of the analyte. In such a way novel photometer devices automatically determine and indicate the concentration of analytes in such multi-assay plates directly without employing a standard curve.

Generally, the methods and devices of the invention rely on separately determining light absorption by the solvent and, at a different wavelength, light absorption by the analyte. Devices for carrying out the methods particularly advantageously include vertical-beam absorbance photometers containing samples disposed within the wells of multi-assay plates, wherein the photometer is able to monitor light absorption of each sample at multiple wavelength bands, including bands in the visible or UV-visible region of the spectrum, as well as bands in the near-infrared region of the electromagnetic spectrum.

The invention, however, is not limited to photometers that measure light absorption solely. Rather the invention is useful generally in vertical-beam photometers that measure optical characteristics in samples where the optical pathlength through a sample is not known but where it is desirable to know such optical pathlength. The invention will find general utility in vertical-beam photometers that, additionally, measure other optical properties of liquid samples, including, but not limited to fluorescence, phosphorescence, chemiluminescence, or light scattering. Thus the invention is useful for chemical measurement by vertical-beam photometers where the measurement is made by either light absorptivity, fluorometry, phosphorometry, chemiluminometry, turbidimetry (where the loss of light from the optical is measured as optical density) and nephelometry (where the light scattered off the optical axis is measured). When utilizing the invention to measure optical properties of samples other than light absorbance, the invention will monitor light absorbance, of the solvent in the sample, in combination with optical properties of the sample other than light absorbance.

From the foregoing it will be appreciated that, although specific embodiments of the invention have been described herein for purposes of illustration, various modifications may be made without deviating from the spirit and scope of the invention.

What is claimed is:

1. A photometric method for determining an optical pathlength of a sample having an analyte dissolved or suspended in an aqueous solvent wherein a relationship between light absorption of the analyte and the optical pathlength of the sample are unknown, the method comprising:

measuring a first light signal resulting from transmission of light, having a first predetermined wavelength, through the aqueous sample, and measuring a second light signal resulting from transmission of light, having a second predetermined wavelength through the aqueous sample, and determining the optical pathlength of the sample from a predetermined relationship between the first and second light signal, and the optical pathlength of the aqueous solvent, wherein the predetermined relationship between the first and second light signals are measured at at about 988–1008 nanometers and about 900–910 nanometers respectively.

2. The method of claim 1 wherein the first and second wavelength are in a near-infrared region of an electromagnetic spectrum of from 750 nanometers to 2500 nanmometers wavelength.

3. A photometric method of determining an optical pathlength of a sample having an analyte dissolved or suspended in an aqueous solvent wherein a relationship between light absorption of the analyte and the optical pathlength of the sample are unknown, the method comprising:

measuring a difference between a first and a second light signal resulting from transmission of light of a first and a second predetermined wavelength, respectively, through the sample, and determining the optical pathlength of the aqueous sample from a predetermined relationship between the difference and a light absorption pathlength of the aqueous solvent, wherein the predetermined relationship between the first and second light signals are measured at at about 988–1008 nanometers and about 900–910 nanometers respectively.

4. A photometric method for determining either a concentration of an analyte, absorbance of an analyte per unit light absorption pathlength, or fraction of light transmitted by an analyte per unit light absorption pathlength, wherein the analyte is suspended or dissolved in a liquid aqueous solvent such that a relationship between light absorption of the analyte and the light absorption pathlength of the analyte are unknown, the method comprising:

measuring a first, a second and a third light signal resulting from, respectively, a first, second and third predetermined wavelength of light transmitted through substantially identical optical pathlengths within a sample and wherein a difference between the first and second light is related to the optical pathlengths and the third light signal is related to both the concentration of the analyte and the optical pathlengths;

measuring a fourth and fifth light signal resulting from, respectively, the first and second wavelengths of light transmitted through a predetermined optical pathlength of the aqueous solvent;

determining a difference in the first and second light signals and a difference in the fourth and fifth light signals; and further determining either the concentration, the absorbance at the third wavelength per unit absorption pathlength, or the fraction of light transmitted at the third wavelength per unit light absorption pathlength, from the predetermined light pathlength, the third light signal, the difference in the first and second light signals and the difference in the fourth and fifth light signals wherein the first and second wavelengths are 985–1008 nanometers and about 900–910 nanometers respectively.

5. A photometric method for determining either a concentration, an absorbance per unit light absorption pathlength, or a fraction of light transmitted per unit absorption pathlength for an analyte suspended or dissolved as a sample in an aqueous solvent wherein neither an optical pathlength or the sample nor its relationship to light absorption of the analyte are known, the method comprising:

measuring a first, a second and a third light signal resulting from, respectively, a first, second and third predetermined wavelength of light transmitted through the sample wherein the first and second wavelengths are 985–1008 nanometers and about 900–910 nanometers respectively, measuring a fourth and fifth light signals resulting from, respectively, the first and second wavelengths of light transmitted through a predetermined optical pathlength of a first reference liquid containing the solvent alone, measuring a sixth, seventh, and eighth light signal resulting from respectively, the first, second and third predetermined wavelength of light transmitted through a predetermined light pathlength of a second reference liquid having the analyte suspended or dissolved in the solvent and determining either a concentration, an absorbance per unit light absorption pathlength, or a fraction of light transmitted per unit light absorption pathlength, of the analyte from the predetermined light pathlength and the first, second, third, fourth, fifth, sixth, seventh, and eighth light signals.

6. A photometric method for determining optical pathlength of an aqueous liquid sample, containing analyte in a solvent, and disposed on a multi-assay plate, the method comprising:

measuring a difference in an amount or fraction of light transmitted, at two different wavelengths, through a reference liquid consisting of the solvent, and contained in a liquid-containing means of known optical pathlength;

measuring a difference in the amount or fraction of light transmitted through the aqueous liquid sample at the first and second wavelengths, wherein for each wavelength the light passes substantially vertically through a meniscus of the sample and wherein the analyte is at concentration unknown with respect to the second reference aqueous liquid wherein the first and second wavelengths are 985–1008 nanometers and about 900–910 nanometers respectively, determining the optical pathlength of the aqueous liquid sample in a multi-assay plate by relating a difference so measured in the liquid sample to the difference so measured in the reference aqueous liquid and to the known optical pathlength wherein the aqueous liquid and the multi-assay plate are maintained at substantially the same temperature.

7. A method for determining a concentration of an analyte in an aqueous liquid sample containing a solvent and disposed in a multi-sample assay plate comprising:

measuring a difference in the amount, or fraction of, light transmitted through a first and a second reference aqueous liquid for each of two different wavelengths wherein the first reference liquid consists of the solvent substantially without the analyte and the second reference liquid consists of the analyte dissolved or suspended in the aqueous solvent and wherein the first and second reference liquids are retained in a liquid containing means of known pathlength;

measuring the amount, or fraction of, light transmitted through the second reference aqueous liquid at a third wavelength;

measuring the amount, or fraction of, light transmitted at the first, second and third wavelengths, substantially vertically through the sample wherein the analyte is present in the aqueous solvent at a concentration unknown with respect to the first or second aqueous liquids, and determining the concentration of the analyte in the aqueous liquid sample by relating the difference to an amount, or fraction of, light transmitted through the sample at the first, second and third wavelengths wherein the first and second wavelengths are 985–1008 nanometers and about 900–910 nanometers respectively.

8. A photometric device comprising a light source for providing at least a portion of a first wavelength range, a wavelength selection means for providing light of a first, a second, and a third wavelength within the first wavelength range, a sample retaining means for retaining one, or more cuvettes of predetermined light absorption pathlength, a sample retaining means for retaining a multi-assay plate, a light-transmitting means for transmitting at least the first and second wavelength through the cuvette(s), a light-transmitting means for transmitting at least the first, second and third wavelength through sample sites on the multi-assay plate, photodetector means for detecting the light transmitted through the cuvette(s) and the light transmitted through the sample sites, a means for relating the light transmitted through the cuvette and the light transmitted through the sample sites additionally comprising a means for determining light absorption pathlength of the samples contained in the multi-assay plate from the relative transmission of the first and second wavelengths of light through the samples and through the cuvette, additionally comprising a means for maintaining the multi-assay plate and the cuvette at substantially the same temperature, wherein the light is transmitted substantially horizontally through the cuvette, so that the light need not pass through a gas-liquid interface when the sample is a liquid, and wherein the light is transmitted substantially vertically through samples contained in the multi-assay plate, so that the light generally will pass through a gas-liquid interface when the samples retained in the multi-assay plate are liquid.

* * * * *